US008900819B2

(12) United States Patent
Chinnaiyan et al.

(10) Patent No.: US 8,900,819 B2
(45) Date of Patent: Dec. 2, 2014

(54) ADRB2 CANCER MARKERS

(75) Inventors: Arul M. Chinnaiyan, Plymouth, MI (US); Jindan Yu, Ann Arbor, MI (US); Rohit Mehra, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/286,820

(22) Filed: Nov. 1, 2011

(65) Prior Publication Data
US 2012/0046196 A1 Feb. 23, 2012

Related U.S. Application Data

(62) Division of application No. 12/016,498, filed on Jan. 18, 2008, now Pat. No. 8,058,003.

(60) Provisional application No. 60/881,416, filed on Jan. 19, 2007.

(51) Int. Cl.
| | | |
|---|---|---|
| G01N 33/53 | (2006.01) | |
| G01N 33/566 | (2006.01) | |
| C12Q 1/68 | (2006.01) | |
| C07K 16/00 | (2006.01) | |
| C12P 21/08 | (2006.01) | |

(52) U.S. Cl.
CPC ........ *C12Q 1/6886* (2013.01); *C12Q 2600/118* (2013.01); *C12Q 2600/136* (2013.01); *C12Q 2600/158* (2013.01)
USPC ...... 435/7.1; 436/501; 530/387.1; 530/387.7; 530/387.9

(58) Field of Classification Search
None
See application file for complete search history.

(56) References Cited

FOREIGN PATENT DOCUMENTS

| WO | 03012067 A2 | 2/2003 |
|---|---|---|
| WO | 2005106488 A2 | 11/2005 |

OTHER PUBLICATIONS

Yu Jin et al., "Integrative Genornics Analysis Reveals Silencing of Beta-Adrenergic Signaling by Polycomb in Prostate Cancer", Cancer Cell, Nov. 2007, 12(5):419-431.
Ringrose and Paro, "Repair and Genetic Consequences of Endogenous DNA Base Damage in Mammalian Cells" Annual Review Genetics, 2004, 38:413-443.
Mulholland et al, "Regulation of Polycomb Group Complexes by the Sequences-Specific DNA Binding Proteins Zeste and Gaga," Genes Dev 2003 17:2741-2746.
Boyer et al., "Polycomb Complexes Repress Developmental Regulators in Murine Embryonic Stem Cells" Nature 2006 441(7091): 349-53.
Lee et al, "Control of Developmental Regulators by Polycomb in Human Embryonic Stem Cells" Cell 2006 125:301-313.
Rank et al, "Transcription Through Intergenic Chromosomal Memory Elements of the Drosophila Bithorax Complex Correlates With an Epigenetic Switch," Mol Cell Biol 2002 22:8026-8034.
Francis and Kingston, "Mechanisms of Transcriptional Memory" Nature Review: Molecular Cell Biology 2001, 2: 409-421.
Levine et al, "The Core of the Polycomb Repressice Complex is Compositionally and Functionally Conserved in Files and Humans," Mol Cell Biol, 2002 22:6070-6078.
Rastelli et al., "Related Chromosome Binding Sites for Zeste, Suppressors of Zeste and Polycomb Group Proteins in Drosophila and Their Dependence on Enhancer of Zeste Function" EMBO 1993 12:1513-1522.
Kirmizis et al, "Silencing of Human Polycomb Target Genes is Associates With Methylation of Histone H3 LYS 27," Genes Dev. 2004 18:1592-1605.
Cao et al., "Role of Histone H3 Lysine 27 Methylation in Polycomb-Group Silencing" Science 2002, 298:1039-1043.
Kuzmichev et al, "Histone Methyltransferase Activity Associated With a Human Muliprotein Compex Containing the Enhancer of Zeste Protein," Genes Dev. 2002 16:2893-2905.
Czermin et al., "Drosophila Enhancer of Zeste/ESC Complexes Have a Histone H3 Methyltransferase Activity That Marks Chromosomal Polycomb Sites" Cell Oct. 2002, 111:185-196.
Varambally et al, "The Polycomb Group Protein EZH2 is Involved in Progression of Prostate Cancer," Nature 2002, 419:624-629.
Bracken et al, "Genome-Wide Mapping of Polycomb Target Genes Unravels Their Roles in Cell Fate Transitions," Genes Dev 20, 1123-1136, 2006.
Visser et al., "The Polycomb Group Protein EZH2 is Upregulated in Proliferating, Cultured Human Mantle Cell Lymphoma." BR J Haematology 2001 112:950-958.
Bachmann et al, "EZH2 Expression is Associated With High Proliferation Rate and Aggressive Tumor Subgroups in Cutaneous Melanoma and Cancers of the Endometrium, Prostate, and Breast" J Clin Oncol. 2006 24:268-273.
Collett et al, "Expression of Enhancer of Zeste Homologue 2 is Significantly Associated With Increased Tumor Cell Proliferation and is a Marker of Aggressive Breast Cancer," Clin Cancer Res. 2006 12:1168-1174.
Matsukawa et al., "Expression of the Enhancer of Zeste Homolog 2 is Correlated With Poor Prognosis in Human Gastric Cancer ." Cancer Science, 2006 97:484-491.
Raaphorst et al, "Poorly Differentiated Breast Carcinoma is Associated With Increased Expression of the Human Polycomb Group EZH2 Gene," Neoplasia Nov./Dec. 2003 5:481-488.
Kleer et al, "EZH2 is a Marker of Aggressive Breast Cancer and Promotes Neoplastic Transformation of Breast Epithelial Cells," Proc Natl Acad Sci USA, 2003, 100, 11606-11611.
Croonquist & Van Ness, "The Polycomb Group Protein Enhancer of Zeste Homolog 2 (EZH2) is an Oncogene That Influences Myeloma Cell Growth and the Mutant RAS Phenotype" Oncogene 2005 24:6269-6280.

(Continued)

*Primary Examiner* — Teresa E Strzelecka
(74) *Attorney, Agent, or Firm* — Tanya A. Arenson; Casimir Jones, S.C.

(57) ABSTRACT

The present invention relates to compositions and methods for cancer diagnosis, research and therapy, including but not limited to, cancer markers. In particular, the present invention relates to ADRB2 markers for cancer.

2 Claims, 12 Drawing Sheets

(56) References Cited

OTHER PUBLICATIONS

Bracken et al., "EZH2 is Downstream of the PRB-E2F Pathway, Essential for Proliferation and Amplied in Cancer" The EMBO Journal, 2003 22(20):5323-5335.
Bos, "Linking Rap to Cell Adhesion", Curr Opin Cell Biol., Apr. 2005 7(2):123-8.
Bos et al., "RAP1 Signalling: Adhering to New Models" Nat Rev Mol Cell Biol May 2001 2:369-377.
Stork and Schmitt, "Crosstalk Between Camp and Map Kinase Signaling in the Regulation of Cell Proliferation" Trends Cell Biol 2002 12: 258-266.
Daaka, "G Proteins in Cancer: The Prostate Cancer Paradigm" Sci. STKE Jan. 13, 2004 (216):RE2.
Price et a, "RAP1 Regulates E-Cadherin-Mediated Cell-Cell Adhesion," J Biol Chem 2004 279:35127-35132.
De Rooij et al., "EPAC is a RAP1 Guanine-Nucleotide-Exchange Factor Directly Activated by Cyclic AMP" Nature 1998 396:474-477.
Crespo et al., "Dual Effect of B-Adrenergic Receptors on Mitogen-Activated Protein Kinase" J Biol Chem 1995 270:25259-25265.
Cook and McCormick, "Inhibition by Camp of RAS-Dependent Activation of RAF." Science Nov. 12, 1993 262(5136):1069-1072.
Kitayama et al., "A RAS-Related Gene With Transformation Suppressor Activity" Cell 1989 56:77-84.
Thaker et al., "Chronic Stress Promotes Tumor Growth and Angiogenesis in a Mouse Model of Ovarian Carcinoma" Nat Med 2006 12: 939-944.
Bos et al, "The Role of RAP1 in Integrin-Mediated Cell Adhesion," Biochem Soc Trans 2003 31:83-86.
Vander Griend and Rinker-Schaeffer, "A New Look at an Old Problem: The Survival and Organ-Specific Growth of Metastases" Sci STKE 2004, PE3.
Kuiperij et al., "Activation of Foxo Transcription Factors Contributes to the Antiproliferative Effect of Camp." Oncogene 2005 24:2087-2095.
Yan et al., "Beta-Adrenergic Receptor/Camp-Mediated Signaling and Apoptosis of S49 Lymphoma Cells" Am J Physiol Cell Physiol. 2000 279, C1665-1674.
Gioeli et al., "Activation of Mitogen-Activated Protein Kinase Associated With Prostate Cancer Progression" Cancer Res 1999 59:279-284.
Rhodes et al, "Oncomine: A Cancer Microarray Database and Integrated Data-Mining Platform" Neoplasia 2004 6:1-6.
Glinsky et al, "Gene Expression Profiling Predicts Clinical Outcome of Prostate Cancer," J. Clin Invest 2004 113(6):913-923.
Yu et al, "Gene Expression Alterations in Prostate Cancer Predicting Tumor Agression and Preceding Development of Malignancy," J. Clin Oncol. 2004 22:2790-2799.
Huang et al, "Gene Expression Predictors of Breast Cancer Outcomes," Lancet 2003 361:1590-1596.
Van't Veer et al, "Gene Expression Profiling Predicts Clinical Outcome of Breast Cancer" Nature 2002 415:530-536.
Tan et al, "Pharmacologic Disruption of Polycomb-Repressive Complex 2-Mediated Gene Repression Selectively Induces Apoptosis in Cancer Cells," Genes Dev 2007 21:1050-1063.
Varambally et al, "Intergrative Genomic and Proteomic Analysis of Prostate Cancer Reveals Signatures of Metastic Progression," Cancer Cell 2005 8:393-406.
Ramaswamy et al, "Multiclass Cancer Diagnosis Using Tumor Gene Expression Signatures," Proc Natl Acad Sci USA, 2001, 98, 15149-15154.
Yang J. et al. Transcriptional and posttranscriptional regulation of beta2-adrenergic receptor gene in rat liver during sepsis, Am. J. Physiol., Jul. 1999, vol. 271 (No. I Pl. 2, pp. R132-R139.
Dorsam, RT et al., Nature Reviews, Cancer, vol. 7, pp. 79-94 (2007).
Schuller, H.M., Cancer Res., vol. 59, pp. 4510-4515 (1999).
Thacker, P.H. et al., Nature Med., vol. 12, pp. 939-944 (2006).
Chaib et al., "Profiling and verification of gene expression patterns in normal and malignant human prostate tissues by cDNA microarray analysis." Neoplasia. Jan.-Feb. 2001; 3(1):43-52.

```
                              SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
cctgggtatt ccagttccag                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cagggtttga tttcccatgt                                                   20

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
ttcctctttg catggaattt g                                                 21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
agaggagtgg gggaagagtc                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tgcaccacca actgcttagc                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthetic
```

```
<400> SEQUENCE: 6
ggcatggact gtggtcatga g                                         21

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gcagagctct ccgtagtcag                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aacaggctgg ggccatacag                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
aggcaccttc tgttggccga                                           20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
aggcagctgc ctcccgtaca                                           20

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
agtgtggtcc tgcgacttct aag                                       23

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12
cctgggcttg agaggtagag tgt                                       23
```

ADRB2 CANCER MARKERS

CROSS REFERENCE TO RELATED APPLICATIONS

This application is a divisional of U.S. patent application Ser. No. 12/016,498, now U.S. Pat. No. 8,058,003, filed Jan. 18, 2008, which claims priority to provisional patent application Ser. No. 60/881,416, filed Jan. 19, 2007, each of which are herein incorporated by reference in its entirety.

STATEMENT REGARDING FEDERALLY SPONSORED RESEARCH OR DEVELOPMENT

This invention was made with government support under grant numbers CA97063, CA111275, and CA69568 awarded by the National Institutes of Health and grant numbers W81XWH-05-1-0173, W81XWH-06-1-0224, and W81XWH-07-1-0107 awarded by ARMY/MRMC. The government has certain rights in the invention.

FIELD OF THE INVENTION

The present invention relates to compositions and methods for cancer diagnosis, research and therapy, including but not limited to, cancer markers. In particular, the present invention relates to ADRB2 markers for cancer.

BACKGROUND OF THE INVENTION

Afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer and 39,200 will die in 2001.

Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

When PSA or digital tests indicate a strong likelihood that cancer is present, a transrectal ultrasound (TRUS) is used to map the prostate and show any suspicious areas. Biopsies of various sectors of the prostate are used to determine if prostate cancer is present. Treatment options depend on the stage of the cancer. Men with a 10-year life expectancy or less who have a low Gleason number and whose tumor has not spread beyond the prostate are often treated with watchful waiting (no treatment). Treatment options for more aggressive cancers include surgical treatments such as radical prostatectomy (RP), in which the prostate is completely removed (with or without nerve sparing techniques) and radiation, applied through an external beam that directs the dose to the prostate from outside the body or via low-dose radioactive seeds that are implanted within the prostate to kill cancer cells locally. Anti-androgen hormone therapy is also used, alone or in conjunction with surgery or radiation. Hormone therapy uses luteinizing hormone-releasing hormones (LH-RH) analogs, which block the pituitary from producing hormones that stimulate testosterone production. Patients must have injections of LH-RH analogs for the rest of their lives.

While surgical and hormonal treatments are often effective for localized PCA, advanced disease remains essentially incurable. Androgen ablation is the most common therapy for advanced PCA, leading to massive apoptosis of androgen-dependent malignant cells and temporary tumor regression. In most cases, however, the tumor reemerges with a vengeance and can proliferate independent of androgen signals. The advent of prostate specific antigen (PSA) screening has led to earlier detection of PCA and significantly reduced PCA-associated fatalities. However, the impact of PSA screening on cancer-specific mortality is still unknown pending the results of prospective randomized screening studies (Etzioni et al., J. Natl. Cancer Inst., 91:1033 [1999]; Maattanen et al., Br. J. Cancer 79:1210 [1999]; Schroder et al., J. Natl. Cancer Inst., 90:1817 [1998]). A major limitation of the serum PSA test is a lack of prostate cancer sensitivity and specificity especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., JAMA 274:1445 [1995]). This has resulted in a surge of equivocal prostate needle biopsies (Epstein and Potter J. Urol., 166:402 [2001]). Thus, development of additional serum and tissue biomarkers to supplement PSA screening is needed.

SUMMARY OF THE INVENTION

The present invention relates to compositions and methods for cancer diagnosis, research and therapy, including but not limited to, cancer markers. In particular, the present invention relates to ADRB2 markers for cancer.

In some embodiments, the present invention provides diagnostic, research, and therapeutic methods that target the underexpression of ADRB2 in cancer.

For example, in some embodiments, the present invention provides a method for identifying cancer (e.g., prostate cancer) in a patient, comprising detecting underexpression of Adrenergic Receptor, Beta 2 (ADRB2) compared to normal expression of ADRB2 in a sample (e.g., a biopsy sample) from a patient, wherein detecting in the sample underexpression of ADRB2 compared to normal expression of ADRB2 identifies cancer in the patient. In certain embodiments, the presence of underexpression of ADRB2 in the sample is indicative of metastatic prostate cancer or the risk of metastatic prostate cancer in the sample. In some embodiments, detecting the presence or absence of underexpression of ADRB2 in the sample comprises detecting the level of ADRB2 nucleic acid (e.g., mRNA) in the sample. In some embodiments, detecting the level of ADRB2 mRNA in the sample comprises the use of microarray analysis, reverse transcriptase PCR, quantitative reverse transcriptase PCR, or hybridization analysis. In other embodiments, detecting the presence or absence of underexpression of ADRB2 in the sample comprises detecting the level of ADRB2 polypeptide in the sample.

The present invention further provides a method for identifying risk of clinical failure in a patient, comprising detecting underexpression of Adrenergic Receptor, Beta 2 (ADRB2) compared to normal expression of ADRB2 in a sample from a patient, wherein detecting in the sample underexpression of ADRB2 compared to normal expression of ADRB2 identifies the patient as being at risk of clinical failure. In some embodiments, the clinical failure is an increase in PSA levels (e.g., of at least 0.2 ng ml$^{-1}$ PSA) or recurrence of disease after prostatectomy. In some embodiments, the recurrence of disease after prostatectomy comprises development of metastatic cancer. In some embodiments, detecting the presence or absence of underexpression of ADRB2 in the sample comprises detecting the level of ADRB2 nucleic acid (e.g., mRNA) in the sample. In some embodiments, detecting the level of ADRB2 mRNA in the sample comprises the use of microarray analysis, reverse transcriptase PCR, quantitative reverse transcriptase PCR, or hybridization analysis. In other embodiments, detecting the presence or absence of underexpression of ADRB2 in the sample comprises detecting the level of ADRB2 polypeptide in the sample.

DEFINITIONS

Figure 1:
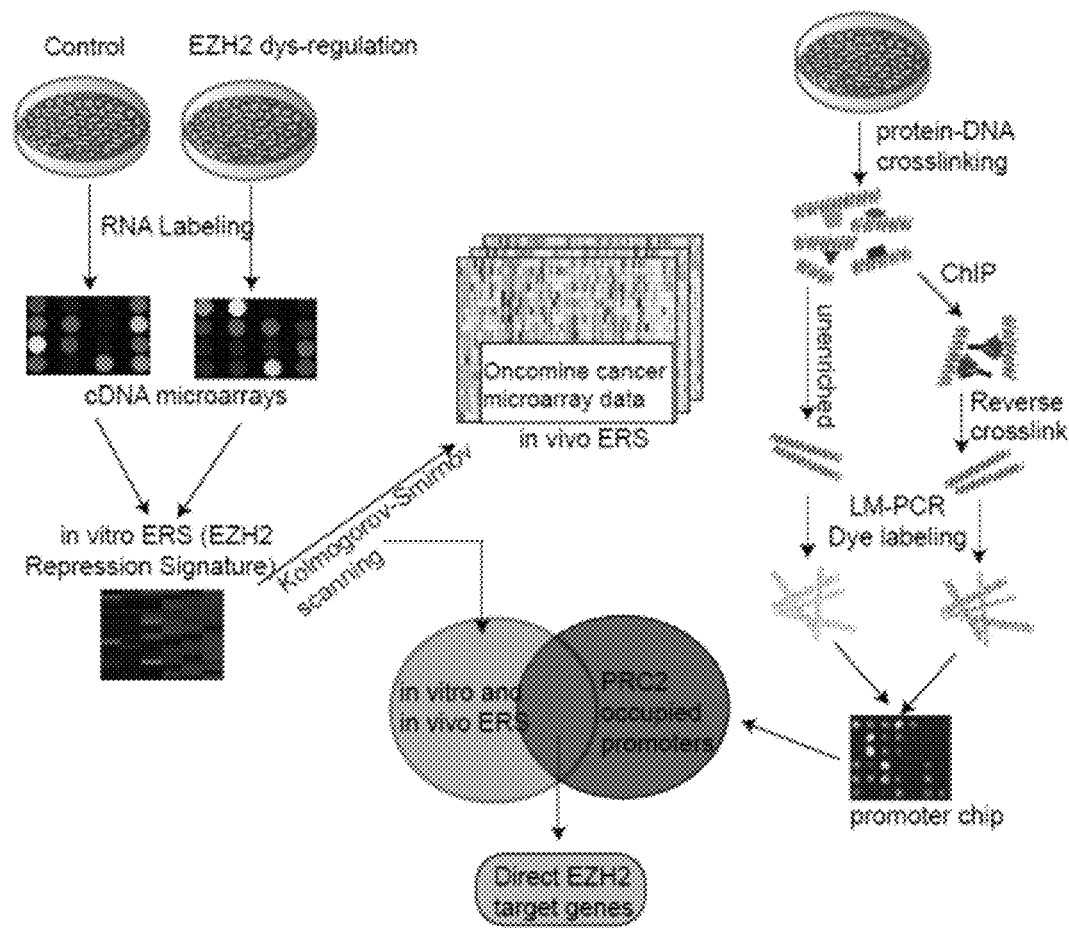
FIG. 1 shows an overview of an integrative genomics analysis used to nominate direct EZH2 transcriptional targets with pathological relevance.

To facilitate an understanding of the present invention, a number of terms and phrases are defined below:

As used herein, the term "underexpression of ADRB2" refers to a lower level of expression of ADRB2 nucleic acid (e.g., mRNA or genomic DNA) or protein relative to the level normally found. In some embodiments, expression is decreased at least 10%, preferably at least 20%, even more preferably at least 50%, yet more preferably at least 75%, still more preferably at least 90%, and most preferably at least 100% relative the level of expression normally found (e.g., in non-cancerous tissue). Expression levels may be determined using any suitable method, including, but not limited to, those disclosed herein.

As used herein, the term "post-surgical tissue" refers to tissue that has been removed from a subject during a surgical procedure. Example include, but are not limited to, biopsy samples, excised organs, and excised portions of organs.

As used herein, the term "biopsy" refers to a tissue sample excised from a subject. Tissue samples may be obtained using any suitable method, including, but not limited to, needle biopsies, aspiration, scraping, excision using surgical equipment, etc.

As used herein, the terms "detect", "detecting", or "detection" may describe either the general act of discovering or discerning or the specific observation of a detectably labeled composition.

As used herein, the term "clinical failure" refers to a negative outcome following prostatectomy. Examples of outcomes associated with clinical failure include, but are not limited to, an increase in PSA levels (e.g., an increase of at least 0.2 ng ml$^{-1}$) or recurrence of disease (e.g., metastatic prostate cancer) after prostatectomy.

The term "RNA interference" or "RNAi" refers to the silencing or decreasing of gene expression by siNAs (e.g., "short interfering RNA", "siRNA", "short interfering nucleic acid molecule", "short interfering oligonucleotide molecule", or "chemically-modified short interfering nucleic acid molecule"). It is the process of sequence-specific, post-transcriptional gene silencing in animals and plants, initiated by siNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner (see, e.g., Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). In some embodiments, the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see, e.g., Martinez et al., 2002, Cell., 110, 563-574 and Schwarz et al., 2002, Molecular Cell, 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. In some embodiments, siNA molecules do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, e.g., Allshire, 2002, Science, 297, 1818-1819; Volpe et aL, 2002, Science, 297, 1833-1837; Jenuwein, 2002, Science, 297, 2215-2218; and Hall et al., 2002, Science, 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region.

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript.

cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The present invention relates to compositions and methods for cancer diagnosis, research and therapy, including but not limited to, cancer markers. In particular, the present invention relates to ADRB2 markers for cancer.

The polycomb group (PcG) proteins are transcriptional repressors important for preserving cellular identity, their most famous targets being the homeotic genes that control the identity of different parts of the segmental body plan (Ringrose and Paro, Annu Rev Genet 38, 413-443 [2004]). PcG target genes are initially repressed by specific transcription factors; this repression is then maintained and passed on by PcG proteins to each new generation of cells through epigenetic modification of chromatin structure (Mulholland et al., Genes Dev 17, 2741-2746 [2003]). In human and mouse embryonic stem cells, PcG proteins contribute to pluripotency and plasticity via repressing developmental transcriptional factors that would otherwise promote differentiation (Boyer et al., Nature 441, 349-353 [2006]; Lee et al., Cell 125, 301-313 [2006]). During differentiation, PcG target genes are selectively activated and cells transition to specialized cell types (Rank et al., Mol Cell Biol 22, 8026-8034 [2002]). Dysregulation of PcG proteins in these cells may disturb transcriptional memory and lead to a lack of differentiation, a hallmark of cancer (Francis and Kingston, Nat Rev Mol Cell Biol 2, 409-421 [2001]).

The PcG proteins function in multiprotein polycomb repressive complexes (PRCs). There are at least two types of PRCs, including PRC1 and PRC2 (Levine et al., Mol Cell Biol 22, 6070-6078 [2002]). These two complexes function in a cooperative manner to maintain epigenetic silencing. PRC1 depends on PRC2, which is essential for the initial binding to target promoters (Rastelli et al., Embo J 12, 1513-1522 [1993]). Core components of PRC2 include SUZ12 (Suppressor of Zest 12), EED (Embryonic Ectoderm Development), and EZH2 (Enhancer of Zest 2) (Kirmizis et al., Genes Dev 18, 1592-1605 [2004]). EZH2 is a histone methyltransferase (HMTase) (Cao et al., Science 298, 1039-1043 [2002]; Kirmizis et al., 2004, supra; Kuzmichev et al., Genes Dev 16, 2893-2905 [2002]) that specifically methylates lysine 27 of histone H3 (H3K27), leading to repression of target gene expression (Czermin et al., Cell 111, 185-196 [2002]; Kirmizis et al., 2004, supra). Studies of PcG silencing in prostate cancer (PCA) indicated that this methylation is mediated by the SET domain of EZH2 and requires histone deacetylase activity (Varambally et al., Nature 419, 624-629 [2002]).

Dysregulation of EZH2 has been associated with a number of cancers including lymphoma, breast cancer, and prostate cancer (Bracken et al., Genes Dev 20, 1123-1136 [2003]; Varambally et al., [2002], supra; Visser et al., Br J Haematol 112, 950-958 [2001]). In addition, EZH2 has been identified as a marker of aggressive epithelial tumors and its up-regulation correlates with poor prognosis (Bachmann et al., J Clin Oncol 24, 268-273 [2006]; Collett et al., Clin Cancer Res 12, 1168-1174 [2006]; Matsukawa et al., Cancer Sci 97, 484-491 [2006]; Raaphorst et al., Neoplasia 5, 481-488 [2003]). For example, expression of EZH2 is significantly higher in metastatic prostate cancer compared with organ-confined prostate tumors (Kleer et al., Proc Natl Acad Sci USA 100, 11606-11611 [2003]; Varambally et al., [2002], supra). In addition, clinically localized prostate cancers that express high levels of EZH2 tend to lead to a poor clinical outcome (Varambally et al., [2002], supra). Functional studies have demonstrated that EZH2 is a bona fide oncogene. EZH2 protein inhibition by RNA interference results in growth arrest in multiple myeloma cells (Croonquist and Van Ness, Oncogene 24, 6269-6280 [2005]) as well as TIG3 diploid human fibroblasts (Bracken et al., Embo J 22, 5323-5335 [2003]). By contrast, ectopic overexpression of EZH2 promotes cell proliferation and invasion in vitro (Bracken et al., [2003], supra; Kleer et al., [2003], supra; Varambally et al., [2002], supra), and induces xenograft tumor growth in vivo (Croonquist and Van Ness, [2005], supra). Some of these oncogenic functions of EZH2 have been shown to require the EZH2 SET domain, suggesting a mechanism involving histone modification and epigenetic silencing. The present invention is not limited to a particular mechanism. Indeed, an understanding of the mechanism is not necessary to practice the present invention.

Nonetheless, it is thus postulated that EZH2 induces tumorigenesis via suppressing key target genes with a role in tumor suppression.

Experiments conducted during the course of development of the present invention employed an integrative genomics approach to identify direct EZH2 targets in the context of cancer from genome-wide expression and location data. One of the target genes identified was ADRB2 (adrenergic receptor beta-2).

ADRB2 is a G-protein coupled receptor (GPCR) of the β-adrenergic signaling pathway. Ligand binding of ADRB2 dissociates G protein subunits and elevates the intracellular level of cyclic adenosine monophosphate (cAMP), a second messenger essential for a wide-range of cellular processes (Bos, Curr Opin Cell Biol 17, 123-128 [2005]). In particular, the cAMP-dependent protein kinase A (PKA) regulates cell growth by multiple mechanisms, one of which is the mitogen-activated protein kinase (MAPK) (also called extracellular signal-regulated kinase, or ERK) cascade (Bos et al., Nat Rev Mol Cell Biol 2, 369-377 [2001]; Stork and Schmitt, Trends Cell Biol 12, 258-266 [2002]). In addition, a recently identified cAMP effector Rap1, a GTPase of the Ras superfamily, has PKA-independent effects on ERK phosphorylation and thus cell proliferation. Furthermore, activation of Rap1 has been shown to regulate cell adhesion and cellular transformation (Price et al., J Biol Chem 279, 35127-35132 [2004]). The role of β-adrenergic signaling in prostate cancer progression, however, has not been investigated. Experiments conducted during the course of development of the present invention found that activating ADRB2 in prostate cancer cells suppresses EZH2-induced cell invasion and epithelial-to-mesenchymal transition (EMT) in vitro, and reduces tumor growth in an in vivo rodent model.

Integrative computational analysis indicated an inverse association between EZH2 and ADRB2 transcript levels in in vitro studies in which EZH2 expression has been experimentally altered as well as in vivo as represented in tumor microarray studies. Using EZH2 adenovirus overexpression, siRNA and shRNA inhibition, it was confirmed that EZH2 represses ADRB2 at both the mRNA and protein levels in a number of prostate and breast cell lines.

There is also a body of evidence demonstrating that EZH2 represses target gene expression via methylation of H3K27 (Cao et al., Science 298, 1039-1043 [2002]). Genome-wide location analysis revealed that a majority of gene promoters occupied by PRC2 complex contain nucleosomes that are also trimethylated at H3K27 (Boyer et al., Nature 441, 349-353 [2006]; Bracken et al., Genes Dev 20, 1123-1136 [2006]; Lee et al., Cell 125, 301-313 [2006]). Experiments conducted during the course of development of the present invention confirmed concordant PRC2 binding and H3K27 trimethylation on the ADRB2 promoter. Further experiments demonstrated that PRC2 complex proteins occupied the ADRB2 promoter at about 0.5 kb and 2 kb upstream of transcriptional start site and trimethylated H3K27 of nearby nucleosomes. PRC2 occupancy on the ADRB2 promoter was robustly detected in a number of cell lines. In 3 out of 3 metastatic tissues examined H3K27 trimethylation on the ADRB2 promoter was observed, indicating epigenetic silencing of ADRB2 in metastatic PCA.

In addition, this study indicates that EZH2 is necessary for PRC2 recruitment and H3K27 trimethylation at the ADRB2 gene promoter. The results also showed that HDAC inhibitors could block this process. This observation provides a mechanism for previous findings indicating that EZH2-mediated transcriptional repression requires HDAC activity (Varambally et al., [2002], supra). The results support the conclusion that HDAC inhibitors find use as therapeutic agents for patients with EZH2-overexpressing tumors.

ADRB2 is a member of the seven-transmembrane receptors, which are often referred to as GPCRs. Ligand binding on ADRB2 strongly increases its affinity with G protein and elevates the level of intracellular cAMP, which modulates cell growth and morphogenesis by multiple mechanisms (Daaka, Sci STKE 2004, re2 [2004]; de Rooij et al., Nature 396, 474-477 [1998]). A hallmark of β-adrenergic signaling is its ability to inhibit cell proliferation in some cell types while stimulating cell growth in others (Stork and Schmitt, Trends Cell Biol 12, 258-266 [2002]). Depending on the cell type, ADRB2 and cAMP may transduce activating or inhibitory signals for cell proliferation and differentiation (Schmitt and Stork, [2002], supra). The most well defined cAMP target associated with cell proliferation is ERK. ERK can be activated or inhibited by cAMP signaling in a cell-context-dependent manner (Crespo et al., J Biol Chem 270, 25259-25265 [1995]). For example, constitutively activated Gα inhibits Ras-dependent proliferation of NIH3T3 and Rat1 fibroblasts through inhibiting growth factor activation of ERKs by blocking Raf-1 activation (Cook and McCormick, Science 262, 1069-1072 [1993]). In a variety of other cell types cAMP activates ERK by Gβγ subunits and B-raf (Crespo et al., [1995], supra; Daaka, Sci STKE 2004, re2 [2004]).

To understand the functional relevance of EZH2 suppression of ADRB2 in prostate cancer, the role of β-adrenergic signaling was investigated in a PCA model system. It was observed that isoproterenol treatment decreased cell invasion whereas ADRB2 inactivation or knockdown induced cell invasion, supporting an inhibitory role of β-adrenergic signaling in prostate cancer progression. This is in line with recent studies showing that cAMP-activated Rap1 controls integrin-dependent processes such as morphogenesis, migration and tumor invasion (Bos et al., Nat Rev Mol Cell Biol 2, 369-377 [2001]). Through Rap1 activation, increased cAMP induces cell adhesion by regulating integrins and E-cadherin (Bos, Curr Opin Cell Biol 17, 123-128 [2005]). The role of β-adrenergic signaling to EZH2 was linked by showing ADRB2 activation rescued EZH2-mediated cell invasion.

Rap1 was initially identified as a transformation suppressor in NIH3T3 by inhibiting the Ras-dependent signaling to Raf-1 (Kitayama et al., Cell 56, 77-84 [1989]). Continuously active Rap1 reverses mesenchymal Ras-transformed Madin-Darby canine kidney cells to an epithelial phenotype (Price et al., J Biol Chem 279, 35127-35132 [2004]). Concordantly, EZH2 expression, hence the potential suppression of ADRB2/Rap1 function, is required for the activated-Ras proliferative phenotype (Croonquist and Van Ness, Oncogene 24, 6269-6280 [2005]). More recently, small RNA interference of EZH2 was found to inhibit DNA synthesis and induce morphological changes in U2OS fibroblasts (Bracken et al., Embo J 22, 5323-5335 [2003]). The association of both upstream and downstream regulators of ADRB2 with cell transformation indicates a role for ADRB2 in this process. Experiments conduted during the course of development of the present invention showed that when ADRB2 expression is constitutively inhibited, prostate cells demonstrated cellular and molecular changes characteristic of EMT. In addition, antagonist inactivation of ADRB2 elicits comparable EMT effects, providing further evidence that β-adrenergic signaling is required for preventing prostate cell transformation. Furthermore, activation of ADRB2 is able to fully reverse molecular changes characteristic of EMT in EZH2 over-expressing cells. The present invention is not limited to a particular mechanism. Indeed, an understanding of the mechanism is not necessary to practice the present invention.

Nonetheless, in is contemplated that these results demonstrate that silencing of the β-adrenergic signaling provides a mechanism for EZH2-mediated tumorigenesis.

EZH2 has been recently shown to act as an oncogene in vivo; overexpression of EZH2 causes xenograft tumor formation in nude mice (Croonquist and Van Ness, [2005], supra). Furthermore, EZH2 catalytic activity is required for cell transformation in vitro and tumor formation in vivo, implicating a role of EZH2-mediated methylation and transcriptional repression in this process. Experiments conducted during the course of development of the present invention demonstrated that DU145 cells with inhibited EZH2 expression do not grow tumors whereas the control cells do. It was examined whether EZH2 target gene ADRB2 has similar function in vivo. Concordantly, it was found that stimulation of ADRB2 receptor in DU145 cells inhibits xenograft tumor growth.

It has also been reported in other cell types, such as ovarian carcinoma, that chronic stress results in tumor growth, potentially involving the concurrent Gα/PKA and Gβγ/MMP pathway (Thaker et al., Nat Med 12, 939-944 [2006]). It is possible that this difference is due to cell-type-specific stimulatory or inhibitory effect of β-adrenergic signaling. In DU145 and RWPE cells, it was shown that ADRB2 activation has inhibitory roles in cell growth and invasion using both in vitro and in vivo assays. It was also observed that along with the inactivation of ADRB2, the phosphorylation of CREB is also reduced. Since CREB phosphorylation is routinely used as a control for PKA activation, this result shows an inhibitory pathway involving $Gα_s$-PKA. In a classic model, the ERK-stimulatory role of cAMP is often mediated through the Gβγ subunits whereas the ERK-inhibitory role by the Gα pathway (Crespo et al., [1995], supra; Daaka, [2004], supra; Stork and Schmitt, [2002], supra). The Gβγ dimers released by GPCR stimulation induce activation of matrix metalloproteinase (MMP), which facilitate Ras-dependent activation of ERK. Data generated during the course of development of the present invention showed that inactivation of ADRB2 inhibits ERK phosphorylation, further supporting an inhibitory role of β-adrenergic signaling. In addition, the antiproliferative effect of cAMP can also be mediated through other mechanisms such as regulation of cell cycle (Bos et al., Biochem Soc Trans 31, 83-86 [2003]; Kuiperij et al., Oncogene 24, 2087-2095 [2005]), without inhibiting ERKs or while activating ERKs. Recent research indicates that tumor cells disseminate early in the process of pathogenesis to widespread sites. To form metastatic lesions, disseminated cells lodged at a secondary site must survive and proliferate by adapting to the foreign microenvironment they encounter (Vander Griend and Rinker-Schaeffer, Sci STKE 2004, pe3 [2004]). One component of this growth is the suppression of stress-induced apoptosis. In S49 lymphoma cells, β-adrenergic/cAMP-mediated signaling induces apoptosis via Gα and PKA (Yan et al., Am J Physiol Cell Physiol 279, C1665-1674 [2000]). In experiments conducted during the course of development of the present invention, DU145 cells were pretreated with isoproterenol prior to injection into mice, which were then treated daily by intraperitoneal injection of isoproterenol.

Using transcript profiling and tissue microarray immunostaining, ADRB2 expression was shown to be considerably down-regulated in metastatic prostate cancer. To test the clinical utility of ADRB2 protein level as a prognostic biomarker of prostate cancer progression, the association of ADRB2 with biochemical recurrence post-prostatectomy was evaluated. It was found that low ADRB2 expression is significantly associated with PSA recurrence. These findings support the ability of ADRB2 to predict clinical outcome and help to select patients at high-risk for aggressive forms of prostate cancer. These results are consistent with the inhibitory role of ADRB2-mediated cAMP signaling in prostate cancer progression. Through analysis of 82 primary and metastatic prostate tumor specimens, activated ERK, which could be an effect of reduction in β-adrenergic signaling, has been associated with prostate cancer progression (Gioeli et al., Cancer Res 59, 279-284 [1999]).

Figure 8:
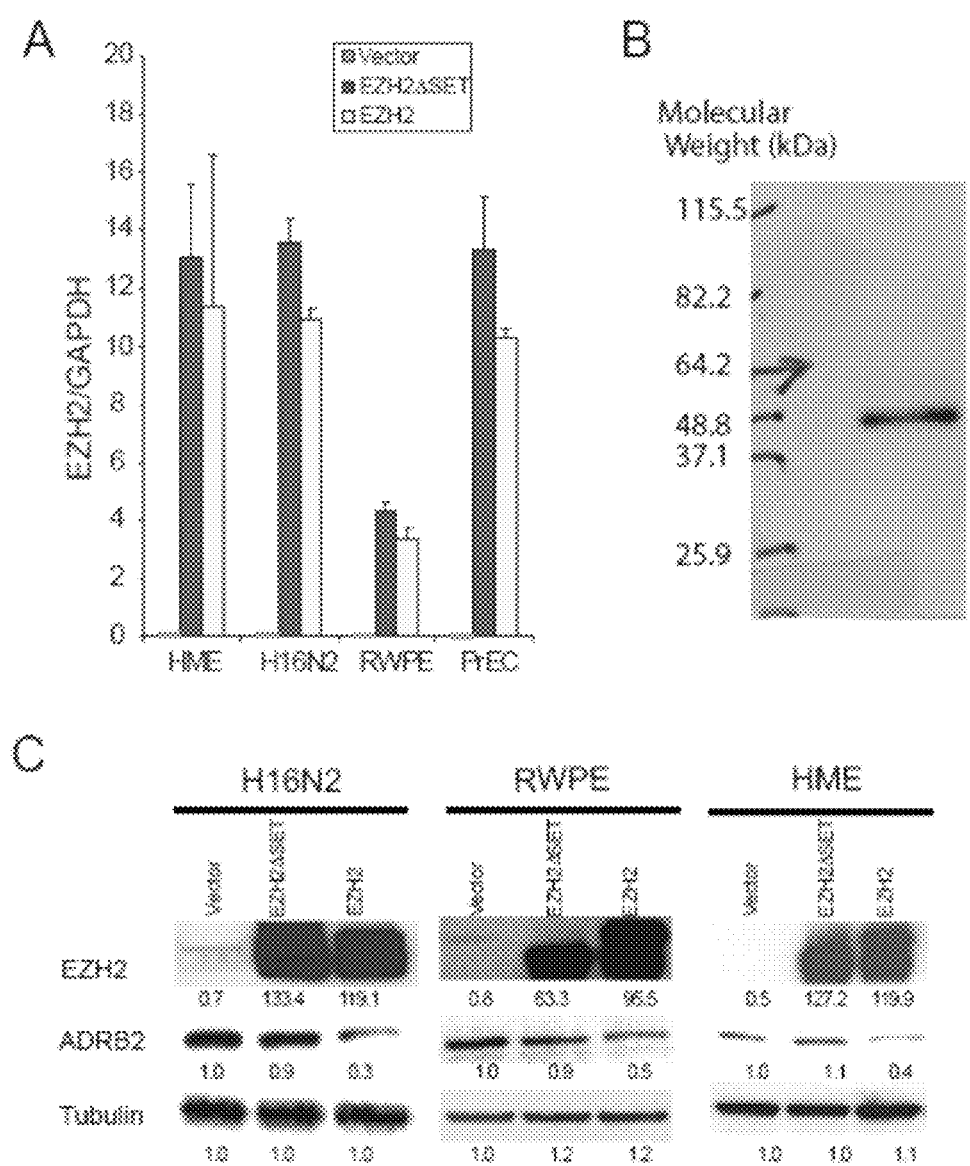
FIG. 8 shows QRT-PCR and immunoblot analysis of EZH2 and ADRB2 following EZH2 overexpression. (A) qRT-PCR analysis of EZH2 transcripts in primary human mammary epithelial cells (HME), and benign immortalized breast (H16N2) and prostate cells (RWPE and PrEC) following infection with vector adenovirus (vector) or adenovirus encoding EZH2 or EZH2ΔSET mutant for 48 hrs. (B) Immunoblot analysis of ADRB2 protein. (C) Immunoblot analysis of EZH2, ADRB2, and β-Tubulin protein levels in benign immortalized breast (H16N2) and prostate cells (RWPE and PrEC) following infection with vector adenovirus (vector) or adenovirus encoding EZH2 or EZH2ΔSET mutant for 48 hrs.

In summary, integrative genomics analysis identified ADRB2 as a direct target of EZH2 transcriptional repression, providing the first PcG target relevant to EZH2's function in tumorigenesis. It is also the first study to demonstrate a functional link between Polycomb group silencing and the β-adrenergic signaling pathway. The present study defined a direct role for ADRB2 in modulating cell invasion, transformation, and tumor growth, possibly by inhibiting Ras-mediated ERK activation through PKA and Rap1 (FIG. 8). It was also demonstrated that ADRB2 is associated with prostate cancer progression in vivo. Clinically, ADRB2 staining in human prostate cancer specimens shows that ADRB2 levels can be used as a prognostic biomarker and to identify patients with aggressive disease (i.e., those with low levels of ADRB2).

I. Cancer Markers

Experiments conducted during the course of development of embodiments of the present invention identified ADRB2 as being underexpressed in epithelial (e.g., prostate and breast) cancers. The present invention thus provides DNA, RNA and protein based diagnostic methods that either directly or indirectly detect underexpression of ADRB2. Some embodiment of the present invention also provide compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

A. Sample

Any patient sample suspected of containing ADRB2 underexpression is tested according to the methods of the present invention. By way of non-limiting examples, the sample may be tissue (e.g., a breast biopsy sample or post-surgical tissue), blood, urine, or a fraction thereof (e.g., plasma, serum, urine supernatant, urine cell pellet or breast cells). In preferred embodiments, the sample is a tissue sample obtained from a biopsy (e.g., needle biopsy, aspiration biopsy or surgically obtained biopsy) or following surgery (e.g., prostate biopsy, lumpectomy or mastectomy).

In some embodiments, the patient sample undergoes preliminary processing designed to isolate or enrich the sample for ADRB2 or cells that contain ADRB2. A variety of techniques known to those of ordinary skill in the art may be used for this purpose, including but not limited: centrifugation; immunocapture; cell lysis; and, nucleic acid target capture (See, e.g., EP Pat. No. 1 409 727, herein incorporated by reference in its entirety).

B. DNA and RNA Detection

In some embodiments, ADRB2 underexpression is detected as mRNA or genomic DNA (e.g., copy number decrease) using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, ADRB1 sequences are detected using fluorescence in situ hybridization (FISH). The preferred FISH assays for the present invention utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

Specific protocols for performing FISH are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT- PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *Bio Technol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified ADRB2 nucleic acids can be detected by any conventional means. For example, in some embodiments, ADRB2 nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

In some embodiments, the present invention provides methods of detecting ADRB2 protein and levels of ADRB2 protein. Proteins are detected using a variety of protein techniques known to those of ordinary skill in the art, including but not limited to: mass spectrometry, protein sequencing, and immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Mass Spectrometry

In some embodiments, mass spectrometry is used to identify proteins. The present invention is not limited by the nature of the mass spectrometry technique utilized for such analysis. For example, techniques that find use with the present invention include, but are not limited to, ion trap mass spectrometry, ion trap/time-of-flight mass spectrometry, time of flight/time of flight mass spectrometry, quadrupole and triple quadrupole mass spectrometry, Fourier Transform (ICR) mass spectrometry, and magnetic sector mass spectrometry. The following description of mass spectroscopic analysis is illustrated with ESI oa TOF mass spectrometry. Those skilled in the art will appreciate the applicability of other mass spectroscopic techniques to such methods.

In some embodiments, proteins are analyzed simultaneously to determine molecular weight and identity. A fraction of the effluent is used to determine molecular weight by either MALD1-TOF-MS or ESI oa TOF (LCT, Micromass) (See e.g., U.S. Pat. No. 6,002,127). The remainder of the eluent is used to determine the identity of the proteins via digestion of the proteins and analysis of the peptide mass map fingerprints by either MALDI-TOF-MS or ESI oa TOF. The molecular weight is matched to the appropriate digest fingerprint by correlating the molecular weight total ion chromatograms (TICs) with the UV-chromatograms and by calculation of the various delay times involved. The resulting molecular weight and digest mass fingerprint data can then be used to search for the protein identity via web-based programs like MSFit (UCSF).

3. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies that are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of ADRB2 expression) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In Vivo Imaging

In some further embodiments, ADRB2 expression is detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence or level of expression of ADRB2 in an animal (e.g., a human or non-human mammal). For example, in some embodiments, ADRB2 mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express ADRB2 at a decreased level relative to the level in non-cancerous tissues (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for ADRB2 are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Compositions for use in the diagnostic methods of the present invention include, but are not limited to, probes, amplification oligonucleotides, and antibodies. Particularly preferred compositions detect the level of expression of ADRB2 in a sample.

Any of these compositions, alone or in combination with other compositions of the present invention, may be provided in the form of a kit. For example, the single labeled probe and pair of amplification oligonucleotides may be provided in a kit for the amplification and detection of ADRB2. The kit may include any and all components necessary or sufficient for assays including, but not limited to, the reagents themselves, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered.

The probe and antibody compositions of the present invention may also be provided in the form of an array.

II. Therapeutic Methods

In some embodiments, the present invention provides methods of customizing cancer (e.g., prostate cancer) therapy. For example, in some embodiments, the presence or absence of underexpression of ADRB2 in a sample from a patient is assayed. Patients with underexpression of ADRB2 are then treated with an therapy that increases the level of ADRB2 (e.g., anti-EZH2 therapy or ADRB2 replacement therapy). The customized treatment methods of the present invention provide the advantage of therapy directed to a specific target at the molecular level. The use of unnecessary treatments that are not effective (e.g., treating a non ADRB2 underexpressing subject with an ADRB2 replacement therapy) can be avoided.

The present invention is not limited to a particular ADRB2 therapy. Exemplary therapies are described below. In some embodiments, known EZH2 antagonists are utilized. In other embodiments, the methods described herein are utilized to identify additional therapeutic compositions.

A. Small Molecule Therapies

In some preferred embodiments, small molecular therapeutics are utilized. In certain embodiments, small molecule therapeutics targeting ADRB2 regulators (e.g., EZH2) are identified, for example, using the drug screening methods of the present invention.

B. Antisense

In some embodiments, the methods involve, for example, the delivery of nucleic acid molecules targeting ADRB2 or ADRB2 pathway component expression and/or activity within cancer cells (e.g., prostate). For example, in some embodiments, the present invention employs compositions comprising oligomeric antisense compounds, particularly oligonucleotides, for use in modulating the function of nucleic acid molecules encoding ADRB2 upstream modulators, ultimately modulating the amount of ADRB2 expressed. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of upstream modulators of ADRB2. In the context of the present invention, "modulation" means either an increase (stimulation) or a decrease (inhibition) in the expression of a gene. For example, expression may be inhibited to potentially prevent tumor growth, inhibition of complement mediated lysis, angiogenesis and proliferation associated with underexpression of ADRB2 (e.g., in prostate cancer).

C. shRNA

In some embodiments, the present invention provides shRNAs that inhibit the expression of ADRB2 upstream modulators (e.g., in prostate cancer cells). A short hairpin RNA (shRNA) is a sequence of RNA that makes a tight hairpin turn that can be used to silence gene expression via RNA interference. shRNA typically uses a vector introduced into cells and utilizes a promoter (e.g., the U6 promoter) to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it.

D. siRNA

In some embodiments, the present invention provides siRNAs that inhibit the expression of upstream modulators of ADRB2 (e.g., in prostate cancer cells). siRNAs are extraordinarily effective at lowering the amounts of targeted RNA (e.g., ADRB2 RNA), and by extension proteins, frequently to undetectable levels. The silencing effect can last several months, and is extraordinarily specific, because one nucleotide mismatch between the target RNA and the central region of the siRNA is frequently sufficient to prevent silencing (see, e.g., Brummelkamp et al, Science 2002; 296:550-3; and Holen et al, Nucleic Acids Res. 2002; 30:1757-66). An important factor in the design of siRNAs is the presence of accessible sites for siRNA binding. Bahoia et al., (J. Biol. Chem., 2003; 278: 15991-15997) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7 mers to 25 mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

E. MicroRNA

In some embodiments, the present invention provides MicroRNAs that inhibit the expression of upstream modulators of ADRB2 (e.g., in prostate cancer cells). MicroRNAs are regulatory, non-protein-coding, endogenous RNAs that have recently gained considerable attention in the scientific community. They are 18-24 nucleotides in length and are thought to regulate gene expression through translational repression by binding to a target mRNA (see, e.g., Lim et al., Science 2003; 299(5612):1540; Chen et al., Semin Immunol 2005; 17(2):155-65; Sevignani et al., Mamm Genome 2006; 17(3):189-202). They are also proposed to regulate gene expression by mRNA cleavage, and mRNA decay initiated by miRNA-guided rapid deadenylation (Wu et al., Proc Natl Acad Sci USA 2006; 103(11):4034-9). miRNAs are abundant, highly conserved molecules and predicted to regulate a large number of transcripts. To date the international miRNA Registry database has more than 600 human identified microRNAs (Griffiths-Jones et al., Nucleic Acids Res 2006; 34 (Database issue):D140-4) and their total number in humans has been predicted to be as high as 1,000 (Berezikov et al., Cell 2005; 120(1):21-4). Many of these microRNAs exhibit tissue-specific expression (Sood et al., Proc Natl Acad Sci USA 2006; 103(8):2746-51) and many are defined to be either tumor suppressors or oncogenes (Lee et al., Curr Opin Investig Drugs 2006; 7(6):560-4; Zhang et al., Dev Biol 2006; Calin et al., Nat Rev Cancer 2006; 6(11):857-66) and play a crucial role in variety of cellular processes such as cell cycle control, apoptosis, and haematopoiesis. Dysregulation of several miRNAs are thought to play a significant role in human disease processes including tumorigenesis (Hwang et al., Br J Cancer 2006; 94(6):776-80; Thomson et al., Genes Dev 2006; 20(16):2202-7).

F. Delivery of Nucleic Acids

Introduction of molecules carrying genetic information into cells is achieved by any of various methods including, but not limited to, directed injection of naked DNA constructs, bombardment with gold particles loaded with the constructs, macromolecule mediated gene transfer using, for example, liposomes, biopolymers, and the like, and ex vivo transfection and/or gene therapy followed by transplantation. The present invention is not limited to a particular approach for introducing molecules carrying genetic information to a subject (e.g., a human subject, a non-human subject). In some embodiments, the methods employ a nanovector delivery system (e.g., a cationic liposome-mediated gene transfer system; a lipoplex) for delivering gene therapeutics to a subject. Current approaches to deliver gene therapeutics to cancer patients often employ either viral or non-viral vector systems. Viral vector-directed methods show high gene transfer efficiency but are deficient in several areas. The limitations of a viral approach are related to their lack of tumor targeting and to residual viral elements that can be immunogenic, cytopathic, or recombinogenic. To circumvent these problems, progress has been made toward developing non-viral, pharmaceutical formulations of gene therapeutics for in vivo human therapy, particularly nanovector delivery systems (e.g., cationic liposome-mediated gene transfer systems). Indeed, there are multiple clinical trials underway using nanovector delivery systems for gene delivery, and liposomes for delivery of chemotherapeutics such as doxorubicin are already on the market for breast cancer chemotherapy. Features of nanovector delivery systems (e.g., cationic liposomes) that make them versatile and attractive include: ease of preparation, ability to complex large pieces of DNA/RNA, the ability to transfect many different types of cells, including non-dividing cells, and the lack of immunogenicity or biohazard activity.

In some embodiments, the nanovector delivery systems (e.g., cationic liposomes) are configured to bear a ligand recognized by a cell surface receptor (e.g., to increase desired targeting to, for example, a tumor). The nanovector delivery systems are not limited to a particular ligand recognized by a cell surface receptor. In some embodiments, the ligand is recognized by a cell surface receptor specific to a tumor. In some embodiments, the ligand is transferrin (Tf). In some embodiments, the ligand is a single chain antibody fragment (scFv) (e.g., specific to Tf). Receptor-mediated endocytosis represents a highly efficient internalization pathway in eukaryotic cells. The presence of a ligand on a nanovector delivery systems (e.g., cationic liposome; lipoplex) facilitates the entry of DNA into cells. Recently, a tumorspecific, ligand-targeting, self-assembled nanoparticle-DNA lipoplex system designed for systemic gene therapy of cancer was developed (see, e.g., U.S. Pat. No. 6,749,863; Tibbetts R S, Genes Dev 2000; 14:2989-3002; Zou L, Science 2003; 300: 1542-1548; each of which is herein incorporated by reference). These nanovector systems employ transferrin (Tf) or a single chain antibody fragment (scFv) against the transferrin receptor which is overexpressed in the majority of human cancers, including pancreatic cancer (see, e.g., Busino L, et al., Nature 2003; 426: 87-91). TfR-scFv-targeted nanovectors were recently approved by the FDA for clinical testing and the first Phase I clinical trial for non-viral systemic p53 gene therapy is ongoing.

Some methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is incorporated herein by reference in their entireties.

G. Antibody Therapy

In some embodiments, the present invention provides antibodies that target tumors that underexpress ADRB2. Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against ADRB2 or an ADRB2 regulator, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., ADRB2 regulators). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

H. Pharmaceutical Compositions

A therapeutic nucleic acid molecule of the present invention can be adapted for use to treat any disease, infection or condition associated with gene expression, and other indications that can respond to the level of gene product in a cell or tissue, alone or in combination with other therapies. For example, a therapeutic nucleic acid molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074), poly (lactic-co-glycolic)acid (PLGA) and PLCA microspheres (see for example U.S. Pat. No. 6,447,796 and U.S. Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. Many examples in the art describe CNS delivery methods of oligonucleotides by osmotic pump, (see Chun et al., 1998, Neuroscience Letters, 257, 135-138, D'Aldin et al., 1998, Mol. Brain Research, 55, 151-164, Dryden et al., 1998, J. Endocrinol., 157, 169-175, Ghimikar et al., 1998, Neuroscience Letters, 247, 21-24) or direct infusion (Broaddus et al., 1997, Neurosurg. Focus, 3, article 4). Other routes of delivery include, but are not limited to oral (tablet or pill form) and/or intrathecal delivery (Gold, 1997, Neuroscience, 76, 1153-1158). More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein. The siNAs of the instant invention can be used as pharmaceutical agents. Pharmaceutical agents prevent, modulate the occurrence, or treat (alleviate a symptom to some extent, preferably all of the symptoms) of a disease state in a subject.

Thus, embodiments of the present invention feature a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes siRNA molecules to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of nucleic acid molecules in the physical location most suitable for their desired activity. Non-limiting examples of agents suitable for formulation with the nucleic acid molecules of embodiments of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly (DL-lactide-coglycolide) microspheres for sustained release delivery after intracerebral implantation (Emerich, D F et al, 1999, Cell Transplant, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies include, but are not limited to, material described in Boado et al., 1998, J. Pharm. Sci., 87, 1308-1315; Tyler et al., 1999, FEBS Lett, 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation based on their ability to avoid accumulation in metabolically aggressive MPS tissues such as the liver and spleen.

Embodiments of the present invention also include compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer. The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphage; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols. Nucleic acid molecules can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In some embodiments, the methods of the present invention directed toward increasing ADRB2 expression and/or activity, further involve co-administration with an anti-cancer agent (e.g., chemotherapeutic). The present invention is not limited by type of anti-cancer agent co-administered. Indeed, a variety of anti-cancer agents are contemplated to be useful in the present invention including, but not limited to, Acivicin; Aclarubicin; Acodazole Hydrochloride; Acronine; Adozelesin; Adriamycin; Aldesleukin; Alitretinoin; Allopurinol Sodium; Altretamine; Ambomycin; Ametantrone Acetate; Aminoglutethimide; Amsacrine; Anastrozole; Annonaceous Acetogenins; Anthramycin; Asimicin; Asparaginase; Asperlin; Azacitidine; Azetepa; Azotomycin; Batimastat; Benzodepa; Bexarotene; Bicalutamide; Bisantrene Hydrochloride; Bisnafide Dimesylate; Bizelesin; Bleomycin Sulfate; Brequinar Sodium; Bropirimine; Bullatacin; Busulfan; Cabergoline; Cactinomycin; Calusterone; Caracemide; Carbetimer; Carboplatin; Carmustine; Carubicin Hydrochloride; Carzelesin; Cedefingol; Celecoxib; Chlorambucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Denileukin Diftitox; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; FK-317; FK-973; FR-66979; FR-900482; Gemcitabine; Geimcitabine Hydrochloride; Gemtuzumab Ozogamicin; Gold Au 198; Goserelin Acetate; Guanacone; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Methoxsalen; Metoprine; Meturedepa; Mitindomide; Mitocarcin; Mitocromin; Mitogillin; Mitomalcin; Mitomycin; Mytomycin C; Mitosper; Mitotane; Mitoxantrone Hydrochloride; Mycophenolic Acid; Nocodazole; Nogalamycin; Oprelvekin; Ormaplatin; Oxisuran; Paclitaxel; Pamidronate Disodium; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rituximab; Rogletimide; Rolliniastatin; Safingol; Safingol Hydrochloride; Samarium/Lexidronam; Semustine; Simtrazene; Sparfosate Sodium; Sparsomycin; Spirogermanium Hydrochloride; Spiromustine; Spiroplatin; Squamocin; Squamotacin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trastuzumab; Trestolone Acetate; Triciribine Phosphate; Trimetrexate; Trimetrexate Glucuronate; Triptorelin; Tubulozole Hydrochloride; Uracil Mustard; Uredepa; Valrubicin; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlorethamine); cyclophosphamide; melphalan; chlorambucil; ifosfamide; busulfan; N-methyl-N-nitrosourea (MNU); N,N-Bis(2-chloroethyl)-N-nitrosourea (BCNU); N-(2-chloroethyl)-N-cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl)ethylphosphonate-N-nit-rosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide; 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); and 2-chlorodeoxyadenosine (2-Cda).

Other anti-cancer agents include: Antiproliferative agents (e.g., Piritrexim Isothionate), Antiprostatic hypertrophy agent (e.g., Sitogluside), Benign prostatic hypertrophy therapy agents (e.g., Tamsulosin Hydrochloride), Prostate growth inhibitor agents (e.g., Pentomone), and Radioactive agents: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 125; Triolein I 131.

Another category of anti-cancer agents is anti-cancer Supplementary Potentiating Agents, including: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

Still other anticancer agents are those selected from the group consisting of: annonaceous acetogenins; asimicin; rolliniastatin; guanacone, squamocin, bullatacin; squamotacin; taxanes; paclitaxel; gemcitabine; methotrexate FR-900482; FK-973; FR-66979; FK-317; 5-FU; FUDR; FdUMP; Hydroxyurea; Docetaxel; discodermolide; epothilones; vincristine; vinblastine; vinorelbine; meta-pac; irinotecan; SN-38; 10-OH campto; topotecan; etoposide; adriamycin; flavopiridol; Cis-Pt; carbo-Pt; bleomycin; mitomycin C; mithramycin; capecitabine; cytarabine; 2-C1-2'deoxyadenosine; Fludarabine-$PO_4$; mitoxantrone; mitozolomide; Pentostatin; and Tomudex. One particularly preferred class of anticancer agents are taxanes (e.g., paclitaxel and docetaxel). Another important category of anticancer agent is annonaceous acetogenin. Other cancer therapies include hormonal manipulation. In some embodiments, the anti-cancer agent is tamoxifen or the aromatase inhibitor arimidex (i.e., anastrozole).

III. Antibodies

ADRB2 or regulator proteins, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures known to those of ordinary skill in the art may be used for the production and labeling of such antibodies and fragments. See, e.g., Burns, ed., *Immunochemical Protocols*, $3^{rd}$ ed., Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975).

V. Drug Screening Applications

In some embodiments, the present invention provides drug screening assays (e.g., to screen for anticancer drugs). The screening methods of the present invention utilize cancer markers identified using the methods of the present invention (e.g., ADRB2). For example, in some embodiments, the present invention provides methods of screening for compounds that alter (e.g., increase or decrease) the expression of cancer marker genes or regulators of cancer marker genes. The compounds or agents may interfere with transcription, by interacting, for example, with the promoter region. The compounds or agents may interfere with mRNA produced from ADRB2 regulators (e.g., by RNA interference, antisense technologies, etc.). The compounds or agents may interfere with pathways that are upstream or downstream of the biological activity of ADRB2. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate cancer.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Mad. Sci. 87:6378-6382 [1990]; Felici, J. Mol. Biol. 222:301 [1991]).

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

VII. Transgenic Animals

The present invention contemplates the generation of transgenic animals comprising an exogenous cancer marker gene (e.g., ADRB2) of the present invention or mutants and variants thereof (e.g., truncations or single nucleotide polymorphisms). In other embodiments, the animals are ADRB2 knockout animals. In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in

*Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

ADRB2 Expression in Prostate Cancer

A. Experimental Procedures
Cell Culture

LNCaP and DU145 prostate cancer cells were cultured in RPMI supplemented with 10% fetal bovine serum (Invitrogen, Carlsband, Calif.). RWPE cells were grown in Keratinocyte-Serum Free medium (Invitrogen) supplemented with 5 ng/ml human recombinant EGF and 0.05 mg/ml bovine pituitary extract. H16N2 immortalized human mammary epithelial cells was grown in Ham's F12 with supplements.

Gene Expression Analysis

Total RNA was isolated at various times after EZH2 infection (RWPE 3, 6, 12, 24, 48, 72 hours; H16N2 6, 12, 24, 48, 72 hours), or at 48 hours after EZH2 RNA interference in both cell lines. Gene expression analysis was done as described using 20 k-element cDNA microarrays covering 15,495 Uni-Gene clusters (Dhanasekaran et al., 2005). The hybridized slides were scanned by Axon scanner (Axon Instruments Inc., Union City, Calif.), and the images analyzed using Genepix and data analyzed as described below.

Chromatin Immunoprecipitation (ChIP) and Genome-Wide Location Analysis

ChIP was performed according to published protocols with slight modifications (Boyd et al., Proc Natl Acad Sci USA 95, 13887-13892 1998). Briefly, formaldehyde was added directly to the cultured cells to a final concentration of 1%. For metastasis tissues, samples were first chopped into small pieces with a razor blade and transferred into 5-10 ml PBS before adding formaldehyde. Cells were rotated at room temperature for 10 min. The crosslinking was stopped by 1/20V of 2.5M Glycine and the cells were washed with 1×PBS and harvested in 1×PBS with proteinase inhibitors. Metastasis tissue samples were further disaggregated using a tissue homogenizer. The cells were then pelleted and resuspended in cell lysis buffer containing protease inhibitors. After incubation in cell lysis buffer for 10 min, the samples were pelleted, resuspended in nuclei lysis buffer and sonicated to chromatins with an average size of 500 bp. The chromatins were precleared using Salmon sperm DNA/Protein A Agarose-50% flurry and incubated with specific antibodies overnight. Antibodies used in this study include EZH2 (BD Bioscience), EED (Upstate), SUZ12 (Abeam), trimethylated H3K27 (Upstate), Acetyl-H3K27 (Upstate), Myc (Abeam), and IgG control (Santa Cruz). The next day, the antibody-bound chromatin was pooled down using protein A/agarose, washed extensively, and reverse-crosslinked. Immunoprecipitated DNA and whole cell extract DNA were purified by treatment with RNase A, proteinase K and purified using Qiaquick PCR purification kit (Qiagen, Valencia, Calif.). The purified DNA was used for PCR analysis of enrichment.

Purified DNA was blunted and ligated to linkers and amplified by a two-stage ligation-mediated PCR (LM-PCR) protocol (Lee et al., Cell 125, 301-313 2006) to generate enough chromatins for PCR analysis of multiple target genes or for hybridization to promoter arrays. Equal amount of amplified input and ChIP-enriched chromatins were subjected to PCR testing for enrichment of target gene promoters.

A total of 200 ng of either whole cell extract DNA or immunoenriched DNA was labeled and purified using BioPrime array CGH genomic labeling kits (Invitrogen, Carlsbad, Calif.). Whole cell extract DNA was labeled with Cy3 dye whereas immunoenriched DNA was labeled with Cy5 dye (Perkin Elmer, Wellesley, Mass.). A total of 2.5 µg each of Cy3- or Cy5-labeled DNA were combined and hybridized at 65° C. for 40 hours to hu6k human proximal promoters (Aviva Systems Biology, San Diego, Calif.) containing a set of 4,839 well-annotated promoters of human genes with clearly defined functions (Li et al., Proc Natl Acad Sci USA 100, 8164-8169 2003).

The hybridized promoter chips were scanned using the GenePix 4000B scanner (Axon, Foster City, Calif.) and analyzed with the GenePix Pro3.0 to extract intensity values and other quality-control parameters. Spot intensity was adjusted by subtraction of the background signal. Features of low intensity (<1000) and bad spots were flagged and excluded from further analysis. Non-flagged features with intensity of 1 standard deviation over background in both channels were included for normalization. The Cy5 and Cy3 channels were normalized by making the mean of the medians-of-Ratios of the normalization features to 1. For all non-flagged features, the normalized median of ratio was taken for further analysis.

From the PC3 cell line, either SUZ12 antibody or IgG control enriched chromatins were hybridized along with input DNA. A gene promoter was considered PRC2 occupied only if the SUZ12/Input intensity ratio was greater than 1.5 and was 0.6 more than the IgG/Input ratio. In the LNCaP cells, a gene promoter was considered PRC2-occupied if the SUZ 12/input ratio was greater than 1.5, since no IgG control chip was done. The sequence named ADRB2 was checked on the promoter array and found to align within 1 kb upstream region of the ADRB2 promoter.

Murine Prostate Tumor Xenograft Model

All procedures involving mice were approved by the University Committee on Use and Care of Animals of the University of Michigan. Male nude athymic BALB/c nu/nu mice 5-week-old (Charles River Laboratory, Wilmington, Mass.) were used for examining the tumorigenicity. To evaluate the role of EZH2−/ADRB2+ DU145-shEZH2 cells in tumor formation, EZH2−/ADRB2+ DU145 cells or the vector control cells were propagated and inoculated by subcutaneous injection into the dorsal flank of 2 groups (5 per group) of mice respectively. To evaluate the role of β-adrenergic signaling in tumor formation, DU145 cell was propagated, and treated with PBS or 10 μM Isoproterenol at 24 hrs prior to harvest. Cells were then harvested and suspended in a 0.1 ml PBS with or without treatment of 10 μM Isoproterenol. A total of 15 mice (n=5 per group) were each implanted with $5 \times 10^6$ DU145 cells into the dorsal flank subcutaneously. Treatment started 24 hrs after implantation. Each group was administered daily by intraperitoneal injection with either PBS or Isoproterenol (at 400 μg/day or 800 μg/day). Tumor size was measured every week and tumor volumes were estimated using the formula $(n/6)(L \times W2)$, where L=length of tumor and W=width.

Gene Expression Analysis

For EZH2 overexpression microarray, total RNA was isolated at various times after EZH2 adenovirus infection (RWPE 3, 6, 12, 24, 48, 72 hours; H16N2 6, 12, 24, 48, 72 hours). For EZH2 RNA interference microarray, the RWPE and H16N2 cell lines were plated at 2.0E05 cells per well in a 12-well plate. Twelve hours after plating, the cells were transfected with 60 pmol of siRNA duplex, sense or antisense oligonucleotides using oligofectamine (Invitrogen). A second identical transfection was performed 24 h later. Total RNA was isolated from each of three cultures of RWPE or H16N2 and transfected for 48 hours with siRNA complexes for either EZH2 or luciferase control.

Gene expression analysis was done as described using 20 k-element cDNA microarrays covering 15,495 UniGene clusters (Dhanasekaran et al., Faseb J 19, 243-245 2005). The hybridized slides were scanned by Axon scanner (Axon Instruments Inc., Union City, Calif.), images analyzed using Genepix and data analyzed as described in detail below. Gene expression values were log-transformed. Two-sample t-tests were performed to determine significant differences in mean gene mRNA expression levels between groups of samples. Expression data from both cell lines were pooled into two groups: EZH2 adenovirus or EZH2 siRNA dataset. For the EZH2 adenovirus and EZH2 RNAi profile datasets, expression values were normalized within each cell line to standard deviations from the mean. In either the EZH2 RNAi or adenovirus datasets, transcripts with less than four non-flagged values for either cell line were filtered from the respective dataset. Only the set of probes (10,444 probes) that has passed the minimal intensity and quality control filters in both datasets was selected for further analysis. For the EZH2 adenovirus dataset, the Pearson correlation coefficient was used to determine the significance of similarity or dissimilarity in expression of each gene with EZH2. For the EZH2 RNAi dataset, two sample t-tests compared profiles of EZH2 RNAi-transfected cells with profiles of RNAi control-transfected cells. False Discovery Rates (FDR) were estimated using the method by (Storey and Tibshirani, 2003). Visualization of gene expression patterns as color maps was obtained using the Cluster and TreeView software (Eisen et al., Proc Natl Acad Sci USA 95, 14863-14868 1998).

Integrative Genomics Analysis

The common set of genes that are repressed by EZH2 overexpression as well as derepressed by EZH2 inhibition was designated as an in vitro EZH2 Repression Signature (ERS). The significance of coordinate expression of the set of EZH2 in vitro-regulated genes within in vivo tissues was determined in the following way. The common population of genes represented in a given profile dataset of in vivo tissues and in the EZH2 adenovirus and RNAi profile datasets were ranked based on a particular metric applied to the expression values in the in vivo dataset (breast and prostate cancer datasets, by inverse correlation with EZH2 expression; Novartis GeneAtlas, by t-statistic comparing adult profiles over fetal profiles; Global Cancer Map, by t-statistic comparing solid tumors over blood tumors). A mapping between cDNA and Affymetrix or Agilent microarray platform was made using common gene names. If a gene was represented more than once on a given platform, then the highest ranking for the gene was used. The significance of the positions of the in vitro ERS genes within the ranked list was evaluated using the Kolmogorov-Smirnov (KS) statistic as described in (Lamb et al., Cell 114, 323-334), with its significance being calibrated using 1000 gene rankings based on random permutations of the sample labels or EZH2 transcript values in the in vivo dataset.

To select a focused subset of genes with the strongest repression by EZH2 in cancer, the expression patterns of individual genes were evaluated in association with EZH2 across multiple datasets. From each of the prostate and breast tumor datasets examined, samples were selected for which EZH2 expression was either very high or very low (>1 SD or <−1 SD) relative to the average expression across all samples within the given dataset. A subset of in vitro ERS genes whose expression patterns showed inverse association with EZH2 were then selected and defined as in vivo ERS.

These in vivo ERS genes were then compared to PRC2 target genes identified by ChIP-on-chip assays. Finally, in vivo ERS genes that are also physically occupied by PRC2 were nominated as "direct EZH2 targets in cancer".

Chemical Reagents

The ADRB2 antagonist ICI 118,551, and agonist Isoproterenol was purchased from Sigma-Aldrich, and used at a working concentration of 1 μM, 10 μM or 100 μM. SAHA was obtained from Biovision Inc, dissolved in DMSO, and used at a working concentration of 1 μM. DZNep was used at 5 μM and cells were treated for 48 hrs before being harvested for RNA isolation.

Cell Culture

LNCaP and DU145 prostate cancer cells were cultured in RPMI supplemented with 10% fetal bovine serum (Invitrogen, Carlsband, Calif.). RWPE cells were grown in Keratinocyte-Serum Free medium (Invitrogen) supplemented with 5 ng/ml human recombinant EGF and 0.05 mg/ml bovine pituitary extract. H16N2 immortalized human mammary epithelial cells was grown in Ham's F12 supplemented with 0.5 μg/ml fungizone, 5 μg/ml gentamycin, 5 mM ethanolamine, 10 mM HEPES, 5 μg/ml transferrin, 10 μM T3, 50 μM selenium, 5 μg/ml insulin, 1 μg/ml hydrocortisone, and 10 ng/ml EGF.

EZH2 adenovirus infection and RNA interference were performed as described (Kleer et al., Proc Natl Acad Sci USA 100, 11606-11611 2003; Varambally et al., Cancer Cell 8, 393-406 2002). RWPE cells with stable ADRB2 knockdown were generated by transfection with ADRB2 shRNA constructs (Open Biosystems, Huntsville, Ala.) and selection with puromycin. DU145 cell lines with stable EZH2 knockdown were generated using EZH2 shRNA expressing constructs (Open Biosystems).

For ChIP and qRT-PCR analysis, DU145 cells were treated with 0.5 μM of SAHA for 30 min, 2, 6, 12 and 24 hrs prior to harvest.

Modified Basement Membrane Assay

Basement membrane matrix invasion assay was essentially performed as previously described (Kleer et al., 2003, supra). Briefly, warm serum free medium was mixed with Matrigel (Fisher Scientific) at 1:3 ratio, 300 μl of this Matrigel mixture was added into the center of each cell well inserts of the Chemicon 24-well plate (Chemicon), and allowed to solidify at room temperature for 1-2 hrs. Cells were trypsinized and resuspended in serum-free medium. Approximately $1 \times 10^5$ cells in 300 μl of serum free medium were placed into each insert, the upper chamber, whereas 500 μl of full medium was added to the lower chamber. Cells were treated with corresponding drug for 10 min prior to be placed into invasion chambers. Cells were then grown in the upper chamber for 48 hrs. The non-invading cells inside the insert were removed and the insert were stained for invaded cells on the lower surface of the membrane. The stained cells were then counted using a microscope and images taken.

Cell Migration Assay Using Scratch Wound Healing

RWPE vector and ADRB2 knockdown cells were grown to confluence. An artificial wound was created using a 10 μl pipette tip on confluent cell monolayer. To visualize migrated cells and wound healing, cell images were taken at 0, 24, and 48 hrs.

Quantitative Real-Time PCR (qRT-PCR)

SYBR green qRT-PCR was carried out according to standard protocols in triplicates (Kleer et al., 2003, supra). Samples were normalized to the mRNA level of the housekeeping gene GAPDH or RPL13A. Primer sequences used are listed in Table 6.

Immunoblot Analysis

Cell extracts were separated by SDS-PAGE and blotted onto nitrocelllular membranes, immunoblotted with antibodies and visualized using ECL-plus (Amercham Bioscience). The following antibodies were used: ADRB2 (Abcam), β-tubulin (Santa Cruz), EZH2 (BD Bioscience). The anti-ADRB2 antibody usually gives a major band of predicted size (46.5 kDa). However, some lots of this antibody may give an extra, weaker band about 5 kDa above the predicted band.

Immunofluorescence Co-Staining

Confocal immunfluorescence co-staining was performed using anti-ADRB2 and anti-EZH2 as previously described (Rhodes et al., Nat Biotechnol 23, 951-959 2005).

Tissue Microarray Analysis (TMA)

TMA of ADRB2 expression in prostate cancer was performed according to established protocols (Varambally et al., Cancer Cell 8, 393-406 2005). For Kaplan-Meier analysis, clinical failure was defined as either an increase of 0.2 ng ml-1 PSA or recurrence of disease after prostatectomy, such as development of metastatic cancer. ADRB2 protein level in each sample was measured based on its product score, which is a product of ADRB2 staining intensity measure at the levels of 1, 2, 3, and 4, and the percentage of positive staining measure ranged from 0-100 percent.

B. Results

Identification of ADRB2 as a Direct Target of EZH2 in Prostate Cancer

The purpose of this study is to characterize key direct targets of EZH2 that confer its oncogenic properties. As EZH2 may regulate a large number of downstream molecules, multiple diverse genomic data were utilized and a number of inclusion criteria were applied for target gene selection, thus minimizing the false positive rates (FIG. 1). To investigate gene expression regulated by EZH2 dysregulation, benign immortalized RWPE prostate and H16N2 breast cell lines were profiled using 20 k-element cDNA microarrays. As described below, 139 features (for 126 unique genes) were identified, defined as an "in vitro EZH2 Repression Signature (ERS)", that are repressed by EZH2 adenovirus overexpression compared to control adenovirus treated cells, as well as up-regulated (derepressed) by EZH2 RNA interference relative to control siRNA-treated cells (Table 3).

Figure 6:
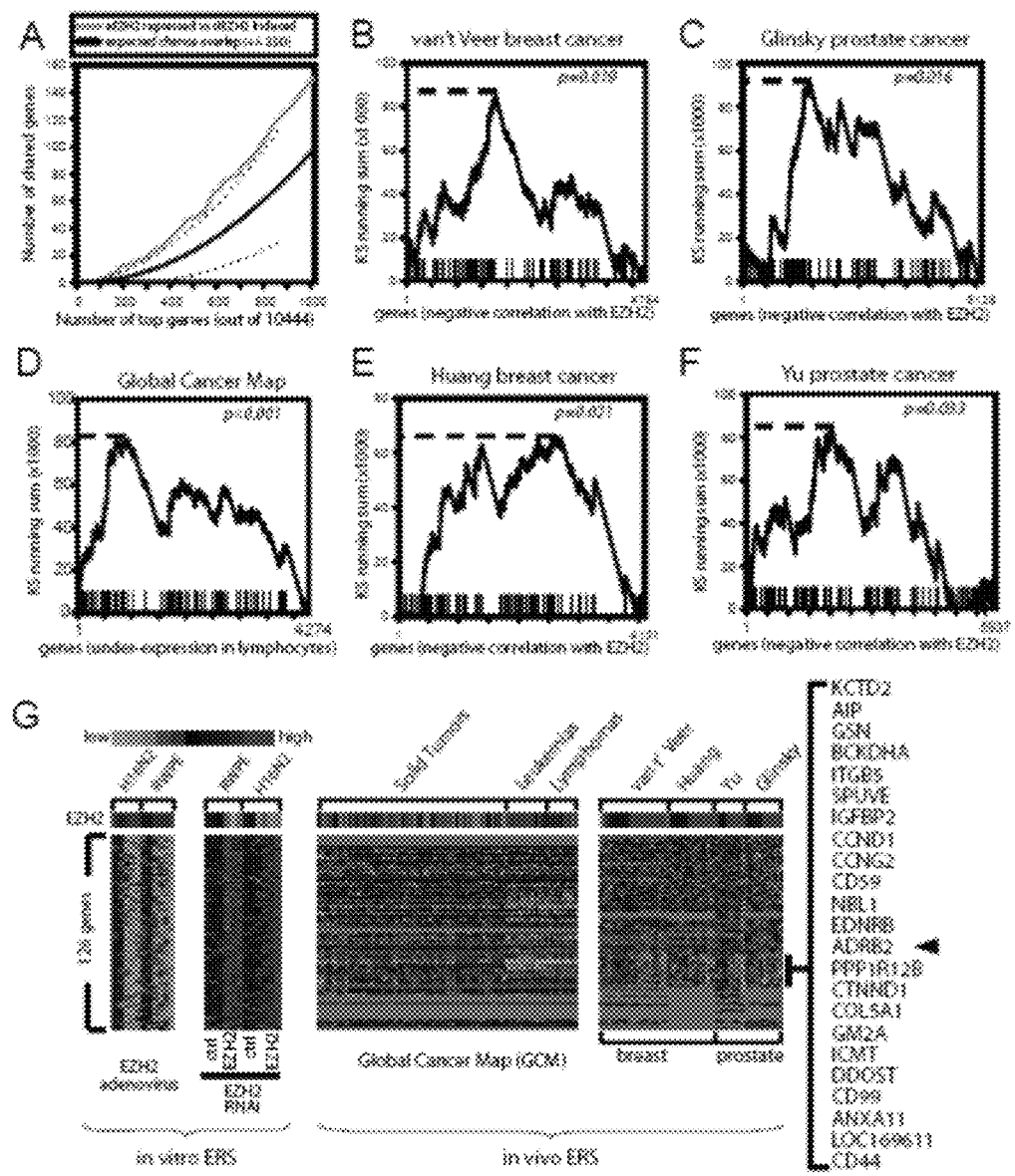
FIG. 6 shows that gene expression analysis identifies putative targets of EZH2 transcriptional repression in vitro and in vivo. (A) Overlap between (1) genes repressed by EZH2 adenovirus (aEZH2) and (2) genes induced by EZH2 RNA interference (siEZH2) is better than chance. (B-F) Putative targets of EZH2 in vitro inversely correlated with EZH2 expression in human tumors and normal tissues in vivo. (G) Expression data matrix of the 126 gene in vitro ERS.

As EZH2 plays a critical role in human cancer progression, EZH2-regulated genes with clinical relevance were investigated. To look for a subset of the in vitro ERS genes with coordinate repression by EZH2 in vivo, several public gene expression datasets of human tumors from Oncomine (Rhodes et al., Neoplasia 6, 1-6 2004), including 2 prostate (Glinsky et al., J Clin Invest 113, 913-923 2004; Yu et al., J Clin Oncol 22, 2790-2799 2004) and 2 breast cancer datasets (Huang et al., Lancet 361, 1590-1596 2003; van't Veer et al., Nature 415, 530-536 2002), and the Global Cancer Map dataset consisting of 190 primary human tumors (Ramaswamy et al., Proc Natl Acad Sci USA 98, 15149-15154 2001) were interrogated. These cancer profiling datasets were selected because EZH2 is best characterized in prostate and breast cancer. The expression pattern of the in vitro ERS genes as a group showed marked inverse association with EZH2 transcript levels in all datasets (FIG. 6). Out of these, 23 individual genes were significantly down-regulated (p<0.05 by t-test) in tumors with higher levels of EZH2 and thus selected as an "in vivo ERS" for further investigation. A large number of these genes have been previously implicated in cell proliferation and cell adhesion.

Figure 7:
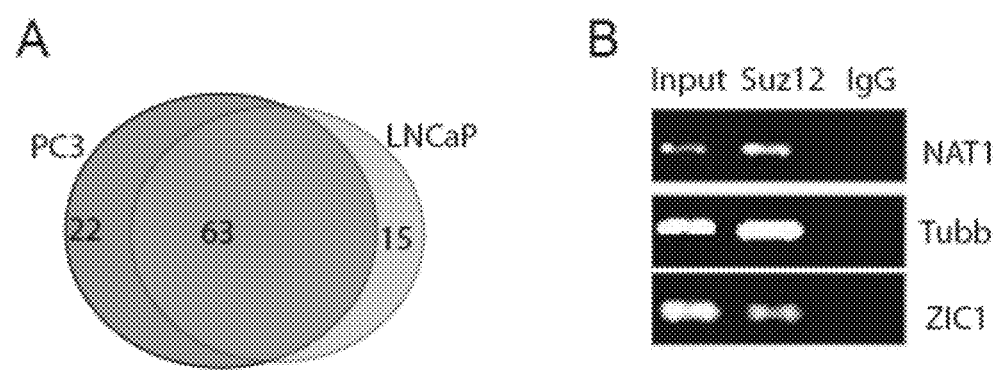
FIG. 7 shows genome-wide location analysis of SUZ12 in the PC3 and LNCaP prostate cancer cells. (A) Venn diagram showing a significant (p<0.0001 by Fisher's exact test) overlap of SUZ12-occupied genes between PC3 and LNCaP cells. (B) Conventional ChIP confirms the enrichment of 3 SUZ12 target genes (NAT1, TUBB, ZIC1) identified by ChIP-on-chip in PC3 cells.

EZH2 is a transcriptional repressor that may regulate downstream gene expression either through direct transcriptional regulation or by subsequent effects. To determine primary targets of EZH2, the genome-wide location of the PRC2 complex was mapped using antibodies against SUZ12, which has been successfully studied for large-scale promoter occupancy (Boyer et al., Nature 441, 349-353 2006; Bracken et al., Genes Dev 20, 1123-1136 2006; Kirmizis et al., Genes Dev 18, 1592-1605 2004; Lee et al., Cell 125, 301-313 2006). Two prostate cancer cell lines, PC3 and LNCaP, were examined to increase the robustness of target genes. 85 PRC2-occupied genes were identified in PC3 cells and 78 in LNCaP. An overlap of 63 genes was observed, demonstrating the accuracy of this assay (Table 4). In a randomly selected set of 3 putative targets (NAT1, TUBB, and ZIC1) was validated by conventional ChIP followed by PCR (ChIP-PCR) assay (FIG. 7).

Gene expression and promoter binding data were compiled in order to identify direct EZH2 targets in prostate cancer. Out of the 23 in vivo ERS genes identified from the transcriptome analysis, 2 genes, namely ADRB2 and IGFBP2, are directly occupied by PRC2.

To identify direct targets of EZH2 in cancer with high confidence, multiple diverse genomics data including in vitro cell line, in vivo tissue expression profiling and genome-wide location data was interogated, as outlined in FIG. 1. In vitro expression profiling was performed with either EZH2 adenovirus overexpression or EZH2 siRNA (short interfering RNA) inhibition in both RWPE prostate and H16N2 breast cell lines. A comparison of top altered genes (ranging from 1 to 1000) from each dataset indicated an overlap that could not be achieved by chance (FIG. 6A). In particular, 577 genes showed significant repression by EZH2 adenovirus ($p<0.05$, false discovery rate (FDR)=0.45) and 2004 showed significant induction by EZH2 siRNA ($p<0.05$, FDR=0.13). Out of these, there is a significant overlap ($p<0.002$ by Fisher's exact test, FDR=0.05) of 139 transcripts (for 126 unique genes) (FIG. 6G & Table 3), thus representing an "in vitro EZH2 Repression Signature (ERS)".

To investigate whether the in vitro ERS genes showed coordinate repression by EZH2 in vivo, thereby demonstrating clinical relevance, public gene expression datasets were examined (Rhodes et al., Neoplasia 6, 1-6 2004) of human tumors. By the Kolmogorov-Smirnov (KS) nonparametric rank statistic (Lamb et al., Cell 114, 323-334 2003), the expression of in vitro ERS as a group showed significant inverse association with EZH2 transcript levels in breast tumors (FIG. 6B with $p=0.019$ for Van't Veer dataset t (van't Veer et al., Nature 415, 530-536 2002), and FIG. 6E with $p=0.021$ for Huang dataset (Huang et al., 2003)), prostate tumors (FIG. 6C with $p=0.016$ for Glinsky dataset (Glinsky et al., J Clin Invest 113, 913-923 2004), and FIG. 6F with $p=0.033$ for Yu dataset t (Yu et al., J Clin Oncol 22, 2790-2799 2004)), and in a group of 190 primary human tumors (FIG. 6D with $p<0.001$ for Global Cancer Map dataset (Ramaswamy et al., Proc Natl Acad Sci USA 98, 15149-15154 2001)). To select a focused subset with the strongest repression by EZH2 in cancer, the expression patterns of individual genes across multiple datasets were examined (FIG. 6G). Of the 126 in vitro ERS genes, 23 were significantly ($p<0.05$ by t-test) down-regulated in tumors with higher levels of EZH2, thus being negatively associated with EZH2 in vivo and representing an "in vivo ERS".

To identify PRC2-occupied gene promoters, the genome-wide location of SUZ12, a PRC2 complex protein that has been successfully studied in embryonic stem Cells was mapped (Boyer et al., Nature 441, 349-353 2006; Bracken et al., Genes Dev 20, 1123-1136 2006; Kirmizis et al., Genes Dev 18, 1592-1605 2004; Lee et al., Cell 125, 301-313 2006). Two prostate cancer cell lines, PC3 and LNCaP, were examined to increase the robustness of target genes. In addition, in order to remove nonspecific binding targets enrichment due to IgG control was evaluated. Eighty five PRC2-occupied genes were identified in PC3 cells and 78 in LNCaP. Out of these, a highly significant ($p<0.0001$ by Fisher's exact test) overlap of 63 genes was observed, thus representing robust PRC2 targets in prostate cancer (Table 4 & FIG. 7). A randomly selected set of 3 putative targets (NAT1, TUBB, and ZIC1) (FIG. 6) was validated by conventional ChIP followed by PCR (ChIP-PCR) assay. In addition, a comparison to SUZ12-occupied genes identified in embryonic stem cells (Lee et al., 2006, supra) revealed a significant ($p<0.001$ by Fisher's exact test) set of common target genes.

The gene expression and promoter binding data was next analyzed in order to identify direct EZH2 targets in cancer. Out of the 23 in vivo ERS genes identified from the transcriptome analysis, 2 genes, namely ADRB2 and IGFBP2, were also PRC2-occupied. Since ADRB2 has been implicated in cell growth and invasion (Bos, Curr Opin Cell Biol 17, 123-128 2005), it was selected for further characterization.

EZH2 Represses Transcript and Protein Levels of ADRB2

Figure 2:
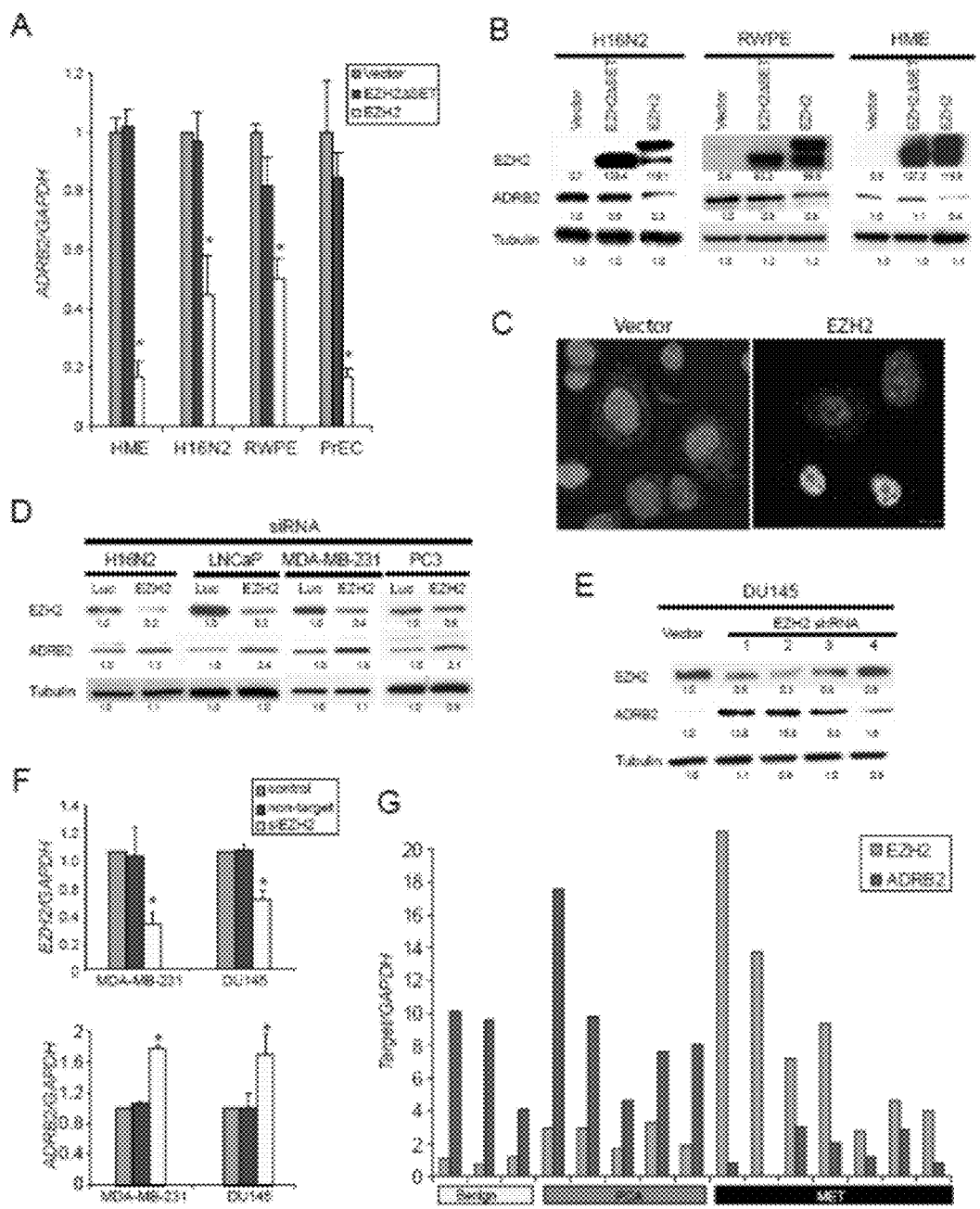
FIG. 2 shows that EZH2 dysregulation negatively regulates ADRB2 transcript and protein. (A) Quantitative RT-PCR analysis for the expression of ADRB2 transcript and (B) Immunoblot analysis of EZH2, ADRB2, and β-tubulin protein in primary human mammary epithelial cells (HME), and benign immortalized breast (H16N2) and prostate cells (RWPE and PrEC) following infection with vector adenovirus (vector) or adenovirus encoding EZH2 or EZH2ΔSET mutant for 48 hrs. (C) Immunofluorescence co-staining of ADRB2 and EZH2 in H16N2 cells following adenoviral infection of control vector or EZH2 for 48 hrs. (D) Immunoblot analysis of EZH2 and ADRB2 expression in multiple cell lines following RNA interference of EZH2 or a control. (E) Immunoblot analysis of ADRB2 and EZH2 in four stable DU145-shEZH2 colonies. (F) QRT-PCR analysis of EZH2 and ADRB2 transcripts in MDA-MB-231 and DU145 cancer cell lines following RNA interference of EZH2 or controls. n=3, mean+SEM. *p<0.01 by t-test. (G) QRT-PCR assessment of ADRB2 and EZH2 expression in prostate tumor specimens.

To confirm that EZH2 represses ADRB2, EZH2 was overexpressed by adenoviral infection of multiple benign prostate and breast cell lines. Quantitative RT-PCR demonstrated significantly reduced levels of ADRB2 transcript in response to EZH2 overexpression relative to adenoviral vector control cells (FIGS. 2A & 8). This downregulation of ADRB2 was not observed with the overexpression of an EZH2 mutant (EZH2ΔSET) lacking the SET domain that is responsible for the HMTase activity of EZH2. To determine whether ADRB2 protein is coordinately regulated, immunoblot analysis of ADRB2 was performed and a major band of predicted size (47 kDa) was observed, supporting the specificity of the antibody (FIG. 8). Consistent with the changes at the transcript level, EZH2 overexpression markedly reduced the expression of ADRB2 protein when compared to the vector and EZH2ΔSET controls, (FIG. 2B). Additionally, to localize ADRB2 and EZH2 proteins in cells, confocal immunofluorescent staining in the H16N2 primary breast cell lines following vector or EZH2 adenoviral infection was performed. ADRB2 staining was found primarily in the cell membrane/cytoplasm whereas EZH2 protein in the cell nucleus (FIG. 2C). In cells infected with EZH2 adenovirus, thus exhibiting strong EZH2 nuclear staining, a marked reduction in ADRB2 staining was observed. By contrast, the vector-infected cells demonstrated absent/low EZH2 and high ADRB2 expression.

ADRB2 is in general expressed at lower levels in prostate cancer cells compared to benign prostate epithelial cells, being opposite or inverse to EZH2. It was hypothesized that this low level of ADRB2 in prostate cancer cells is due to its repression by high EZH2. To test this hypothesis it was examined whether EZH RNA interference can de-repress ADRB2 expression in cell line models. Immunoblot analysis demonstrated up-regulated ADRB2 protein levels in response to transient EZH2 knockdown (FIG. 2D). This up-regulation is more prominent in LNCaP and PC3 prostate cancer cells (over 2 fold) than in primary cell lines (less than 2 fold). As transient RNA interference of EZH2 only moderately induces ADRB2, DU145-shEZH2 cell lines with long-term inhibition of EZH2 was established using short-hairpin RNAs (shRNAs) followed by selection of stable colonies. Stable inhibition of EZH2 led to a marked increase of ADRB2 protein level (FIG. 2E). A strong negative association ($r=-0.98$, $p=0.004$) between EZH2 and ADRB2 protein levels in stable DU145-shEZH2 colonies with varying degree of EZH2 inhibition was observed, thus providing evidence for EZH2-mediated repression of ADRB2. To assure that EZH2 regulation of ADRB2 occurs at the transcript level, ADRB2 and EZH2 transcripts were examined by qRT-PCR. Transient EZH2 RNA interference upregulated ADRB2 mRNA in both the MDA-MB-231 breast and the DU145 prostate cancer cell lines (FIG. 2F).

It was next examined whether this regulation has functional relevance in vivo in human tumors. It was contemplated that that ADRB2 and EZH2 expression are negatively associated in human prostate tumors. To confirm this, their expression was analyzed in a set of 3 benign prostate tissue samples, 5 clinically localized prostate cancers and 7 metastatic prostate cancers by qRT-PCR. The results demonstrated significant overexpression of EZH2 (p<0.001 by Wilcoxon Rank-Sum test), and yet marked downregulation of ADRB2 (p<0.001 by Wilcoxon Rank-Sum test) in metastatic prostate cancer compared to organ-confined disease (FIG. 2G). The expression levels of EZH2 and ADRB2 displayed a strong negative association (r=−0.67, p<0.001) across all samples, consistent with the repression of ADRB2 by EZH2.

The EZH2-Containing PRC2 Complex Occupies the ADRB2 Promoter

Figure 3:
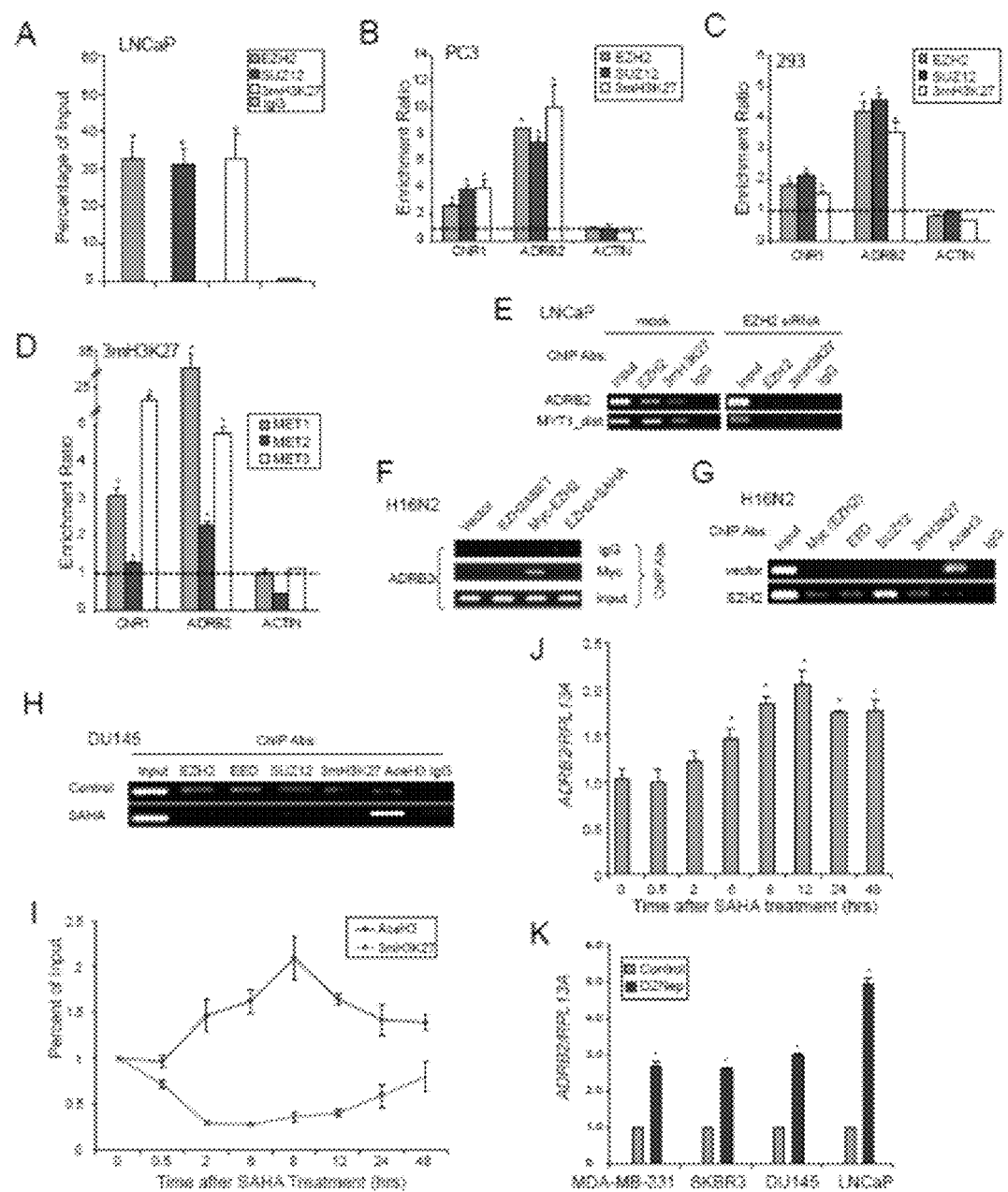
FIG. 3 shows that the ADRB2 promoter is occupied by PRC2 complex proteins and the H3K27 trimethylation (3mH3K27) mark. (A) Conventional ChIP-PCR analysis of EZH2 and SUZ12 occupancy and the level of H3K27 trimethylation (3mH3K27) of the ADRB2 promoter. (B) EZH2, SUZ12 and 3mH3K27 occupancy on the ADRB2 promoter in PC3 metastatic prostate cancer cell line, (C) in 293 embryonic kidney cell line, and (D) in three metastatic prostate cancer tissues (MET1-3). (E) EZH2 RNA interference blocks EZH2 and 3mH3K27 binding to the ADRB2 promoter. (F) Ectopically expressed EZH2 binds ADRB2 promoter in a histone deacetylation dependent manner. (G) Ectopic overexpression of EZH2 increases PRC2 complex occupancy and H3K27 trimethylation, and reduces H3 acetylation at the ADRB2 promoter. (H) Endogenous PRC2 complex occupies the ADRB2 promoter and is sensitive to the HDAC inhibitor SAHA. (I) PRC2 recruitment to the ADRB2 promoter after a time course of SAHA treatment. (J) ADRB2 transcript was up-regulated following SAHA treatment. (K) Marked up-regulation of ADRB2 transcript by the PRC2-inhibiting compound DZNep.

Expression regulation of target genes by a transcription factor or cofactors may be mediated through direct interaction or secondary effects. The genome-wide location analysis suggested that the ADRB2 promoter may be directly occupied by the PRC2 complex protein SUZ12 in LNCaP and PC3 prostate cancer cells. This protein-promoter binding was recapitulated in multiple cancer cell lines as well as in metastatic prostate tumors. LNCaP cells were analyzed by ChIP using antibodies against EZH2, SUZ12, the EZH2-mediated H3K27 trimethylation (3mH3K27), and an IgG antibody control. By conventional ChIP-PCR assay using primers specific to the ADRB2 promoter a strong enrichment (over 30 fold, p<0.001) by EZH2, SUZ12 and 3mH3K27 antibodies relative to the IgG control was observed (FIG. 3A).

It was investigated whether PRC2 binding on the ADRB2 promoter is a robust phenomenon across multiple cell lines in vitro and prostate cancer tissues in vivo. Thus, ChIP analysis was performed in a panel of additional samples including the PC3 prostate cancer cell line, 293 human embryonic kidney cell line, as well as 3 independent metastatic prostate cancer tissues. To provide additional independent evidence a previously reported PRC2 target gene CNR1 (Kirmizis et al., Genes Dev 18, 1592-1605 2004) was analyzed as a positive control and ACTIN as a negative control. ChIP-enriched chromatin was amplified along with whole-cell extract (WCE) DNA to generate enough material for testing multiple target genes. Using an equal amount of amplified WCE and ChIP-enriched DNA, PCR analysis of target genes were evaluated for ChIP-enrichment relative to WCE. The results showed that the PRC2 complex and the 3 mH3K27 mark co-occupy the promoters of ADRB2 and CNR1, but not of ACTIN, in both PC3 (FIG. 3B) and 293 cells (FIG. 3C). The 3 mH3K27 mark was found to occupy the ADRB2 promoter in all 3 metastatic prostate cancer tissues, supporting repression of ADRB2 in vivo (FIG. 3D).

It was next determined whether EZH2 expression is crucial for PRC2 binding and H3K27 trimethylation of the ADRB2 promoter. By combining ChIP-PCR assay with RNA interference in the EZH2-high LNCaP prostate cancer cell, it was found that siRNA inhibition of EZH2 greatly decreased its occupancy and, importantly, also reduced H3K27 trimethylation of the ADRB2 promoter and a positive control (FIG. 3E). Similarly, the effect of EZH2 overexpression on PRC2 recruitment to the ADRB2 promoter was examined in the H16N2 primary breast cell line that expresses low level of endogenous EZH2. An antibody against the Myc-tag of the EZH2 adenoviral constructs for ChIP was used in order to precisely monitor the binding effects of ectopic EZH2. The results demonstrated the recruitment of Myc-EZH2 to the ADRB2 promoter, but not of the vector and the EZH2ΔSET mutant, this binding being sensitive to SAHA, which inhibits HDAC activity and blocks histone deacetylation (FIG. 3F). ChIP showed markedly increased occupancy of other PRC2 complex proteins EED and SUZ12, as well as 3mH3K27 on the ADRB2 promoter, upon EZH2 overexpression relative to vector control, whereas the binding of acetylated H3 was strongly reduced, indicative of increased histone deacetylation (FIG. 3G). Further evaluation of SAHA revealed a marked reduction of PRC2 binding and consequent H3K27 trimethylation, and accumulation of acetylated H3 at the ADRB2 promoter (FIG. 3H-I). QRT-PCR analysis showed corresponding upregulation of ADRB2 transcripts following a time course of SAHA treatment (FIG. 3J).

Tan et al. recently identified an HDAC inhibitor-like small-molecule compound, DZNep, which effectively inhibits the expression of PRC2 complex proteins (Tan et al., Genes Dev 21, 1050-1063 2007). To further confirm that ADRB2 is a transcriptional target of PRC2 the effect of DZNep was examined across a batch of breast and prostate cancer cell lines. The results demonstrated strong induction (de-repression) of ADRB2 in all cell lines tested (FIG. 3K).

Figure 4:
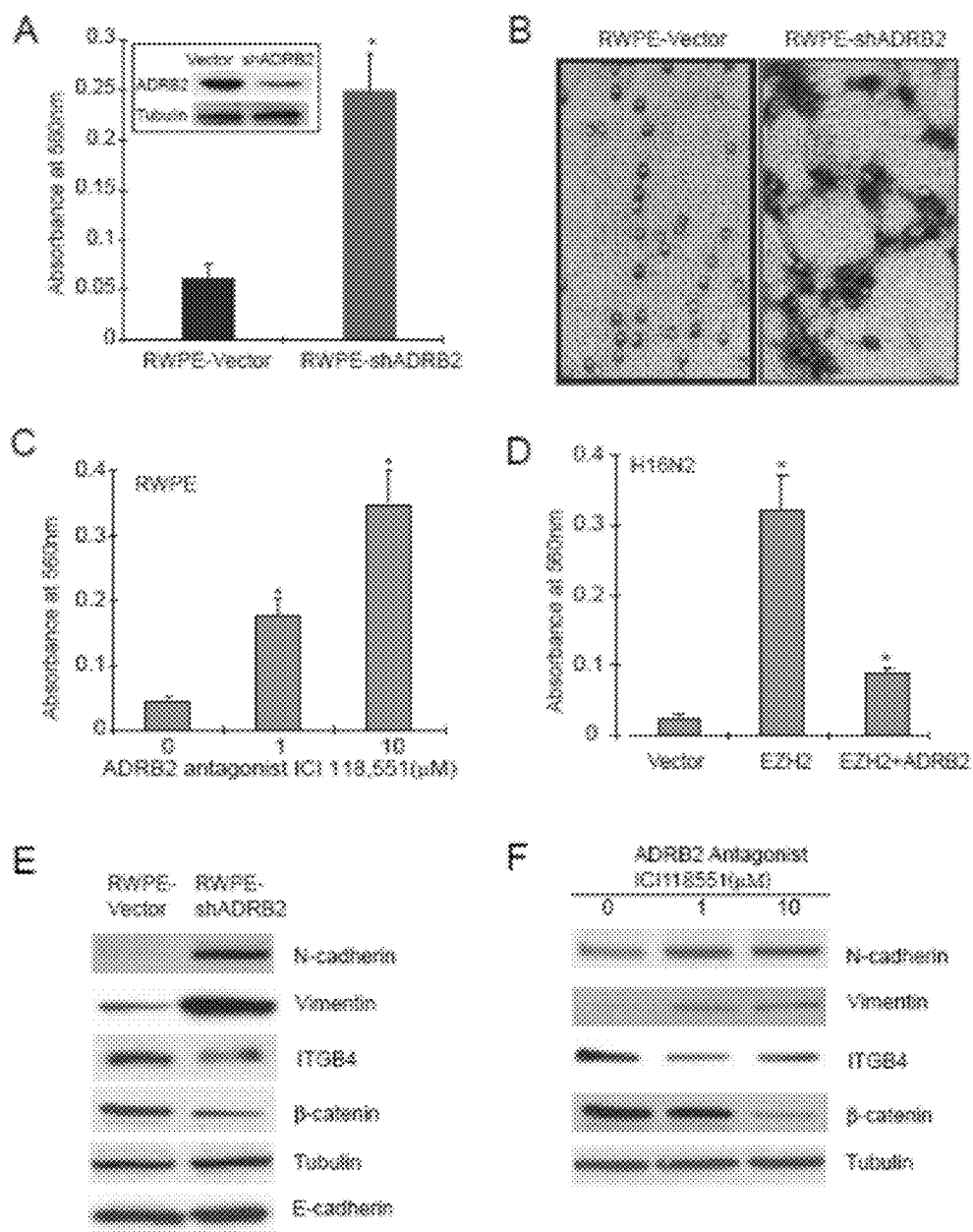
FIG. 4 shows that ADRB2 inhibition confers cell invasion and transforms benign prostate epithelial cells. (A-B) RWPE-shADRB2 cells were assayed for invasion through a modified basement membrane chamber assay. (C) ADRB2 inactivation by antagonist in non-invasive benign RWPE epithelial cells leads to increased invasion. The noninvasive RWPE cells were treated with 0, 1, or 10 μM of an ADRB2-specific antagonist ICI 118,551 and assessed by invasion assay. (D) ADRB2 activation interferes with EZH2-mediated cell invasion. (E-F) ADRB2 inhibition in RWPE benign prostate epithelial cells, either by shRNA targeting ADRB2 (RWPE-shADRB2) or by an ADRB2 antagonist ICI 118,551, regulates the expression of EMT biomarkers and cell adhesion molecules.
Figure 9:
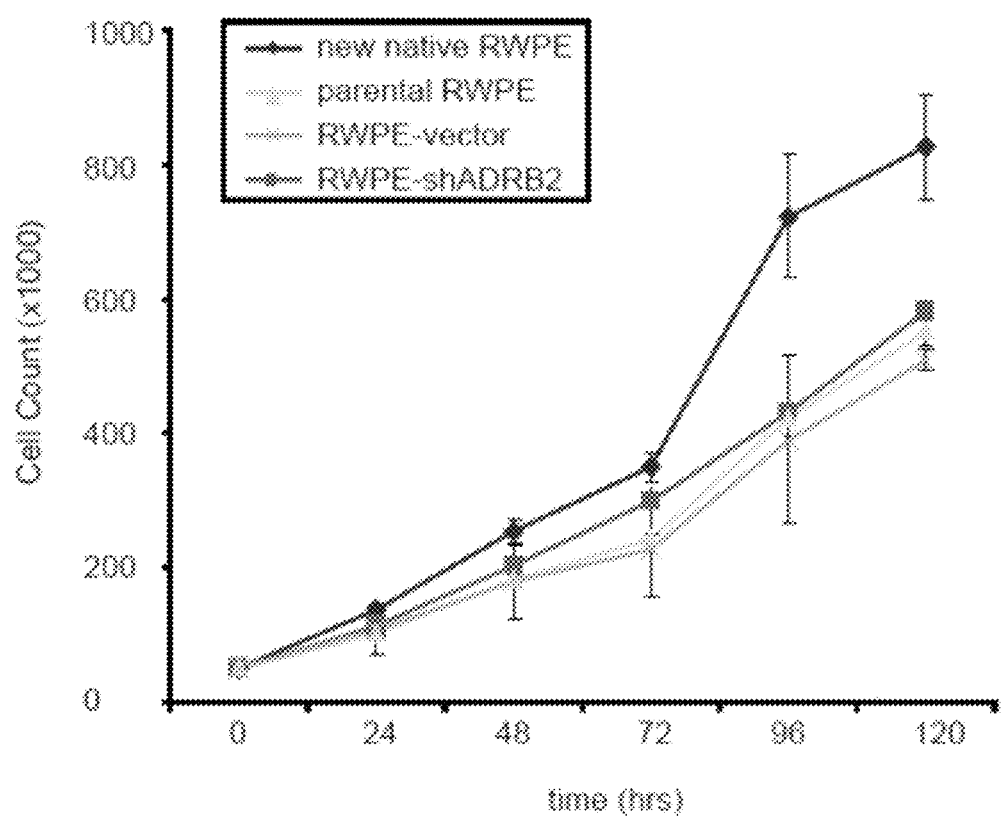
FIG. 9 shows that ADRB2 knockdown does not affect proliferation of benign RWPE prostatic epithelial cells.

ADRB2 Inhibition Confers Cell Invasion and Transforms Benign Prostate Epithelial Cells It was shown above that ADRB2 is a direct target of EZH2 transcriptional repression and is down-regulated in metastatic prostate cancer. Thus, this event was recapitulated in benign prostatic epithelial cells to determine the role of aberrant ADRB2 inhibition in prostate cancer. The immortalized benign prostate epithelial cell line RWPE Was transfected with shRNA constructs targeting ADRB2 and selected for stable RWPE cells with ADRB2 knockdown (RWPE-shADRB2) cells. The stable RWPE-shADRB2 cells showed a marked reduction in ADRB2 expression relative to the vector-transfected control cells (FIG. 4A). The effect of ADRB2 inhibition on various oncogenic properties, such as cell proliferation, invasion and migration was next investigated. The results demonstrate that inhibition of ADRB2 had no significant effect on cell proliferation (FIG. 9). Over 5 fold increase of invasion in RWPE-shADRB2 cells compared to the vector control was observed (FIG. 4A-B). Similarly, inactivation of ADRB2 by the ADRB2-specific antagonist ICI 118,551 significantly increased invasion in RWPE cells (FIG. 4C). Concordant with this, cell migration assay by scratch wound healing showed that the RWPE-shADRB2 cells have markedly increased motility than the vector control cells (FIG. S5). Taken together, these results demonstrate that inhibition of ADRB2 in benign prostate cells confers increased invasion, an important oncogenic phenotype.

Figure 10:
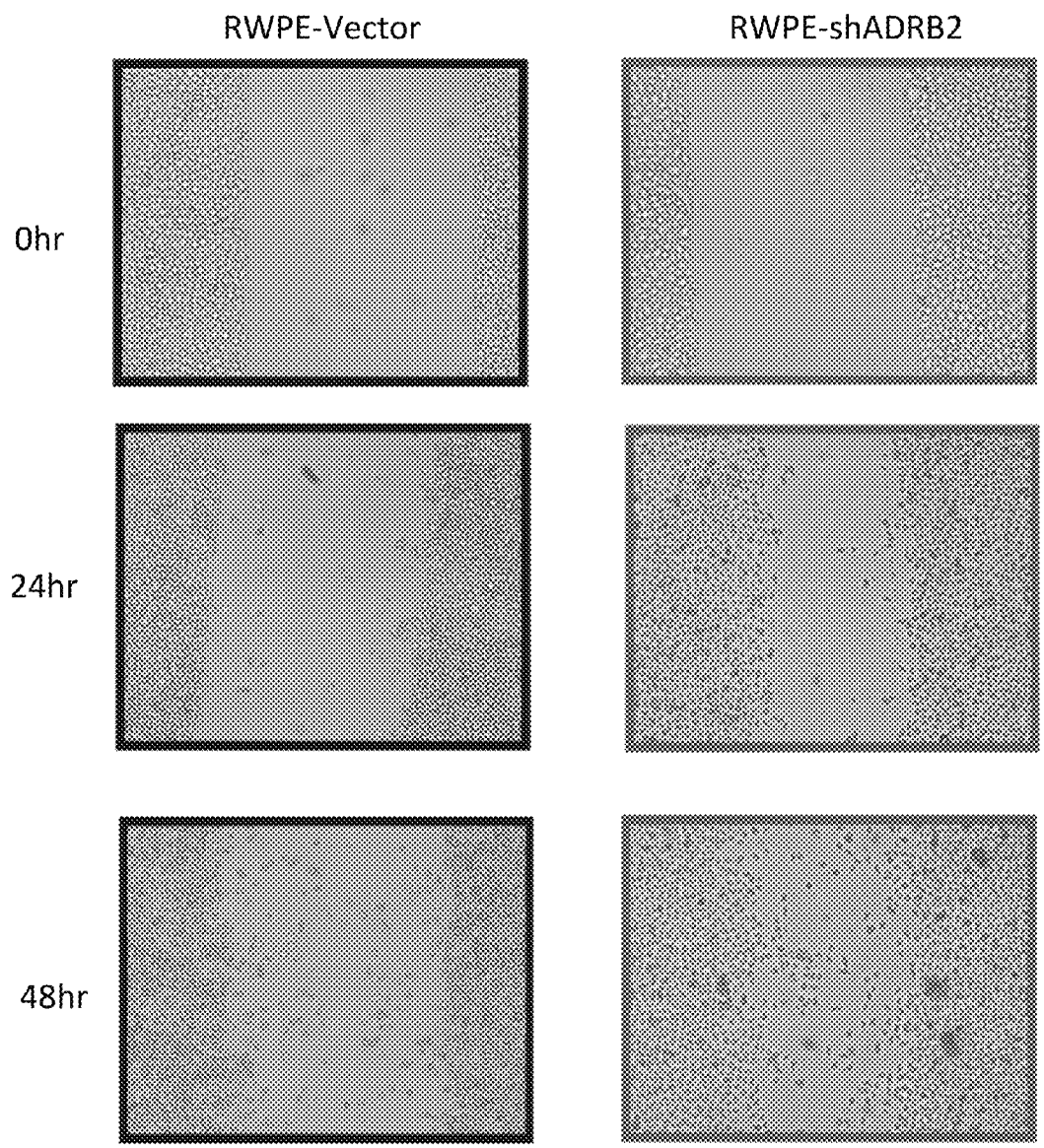
FIG. 10 shows that ADRB2 knockdown markedly increases cell motility in benign RWPE prostatic epithelial cells.
Figure 11:
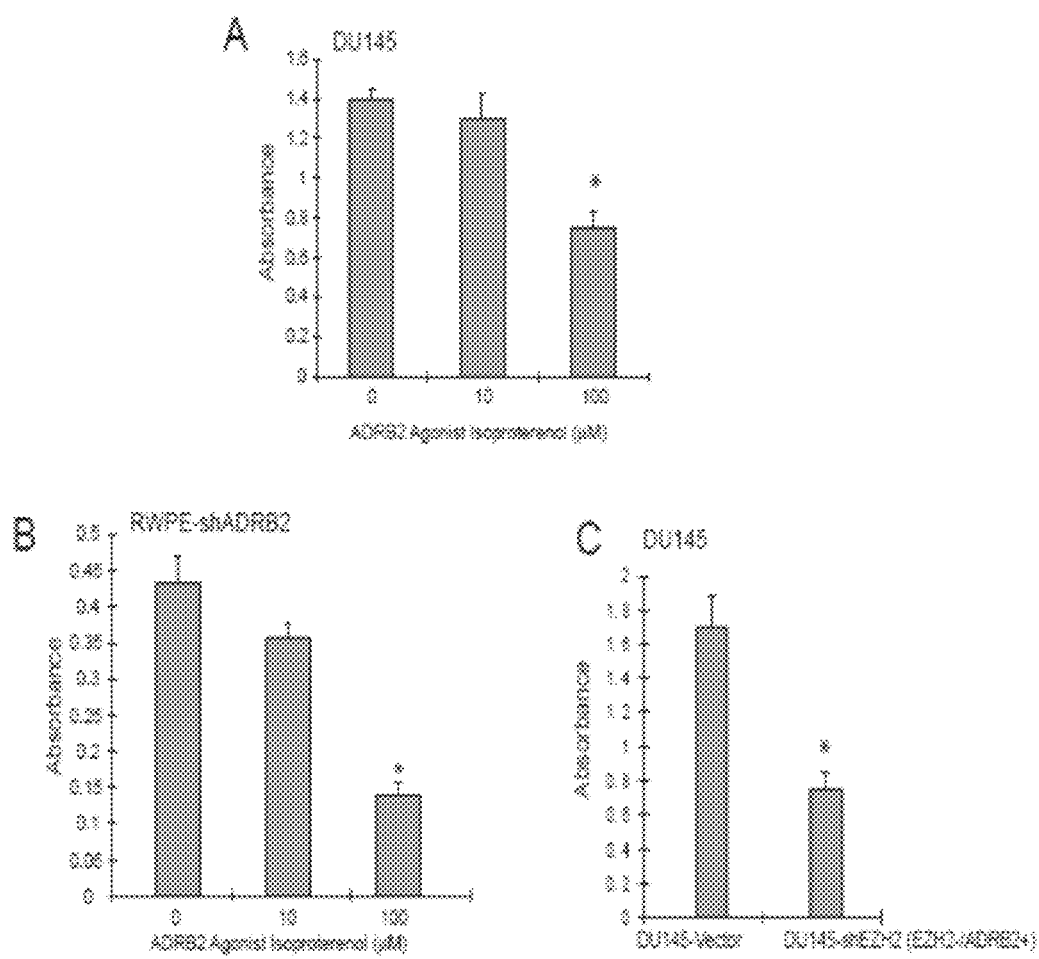
FIG. 11 shows that ADRB2 activation inhibits cell invasion in DU145 and RWPE-shADRB2 cells. (A) DU145 and (B) RWPE-shADRB2 cells were treated with 0, 10, or 100 μM of ADRB2 agonist Isoproterenol and assayed for cell invasion. (C) DU145 prostate cancer cells were treated with vector control or shRNA against EZH2, stable clones were generated and assayed for cell invasion.

To confirm the effect of ADRB2 on cell invasion in additional models, ADRB2 was activated using the agonist isoproterenol in DU145 prostate cancer cells and the invasive RWPE-shADRB2 stable cells. The agonist-activated cells showed significantly reduced invasion in both cell lines (FIG. 10). Concordantly, invasion assays revealed significantly reduced invasion of the DU145-shEZH2 cells with stable EZH2 knockdown and ADRB2 induction.

To directly link ADRB2 expression with oncogenic EZH2 function, it was investigated whether ADRB2 interferes with EZH2-mediated cell invasion. It was previously reported that overexpression of EZH2 increases invasion in immortalized mammary epithelial cell line H16N2 (Kleer et al., 2003, supra). It was investigated whether ADRB2 overexpression is able to rescue this effect by co-transfection of EZH2 and ADRB2. EZH2 overexpression dramatically (12.9 fold, p<0.001) increased invasion in H16N2 cells. By contrast, overexpression of ADRB2 led to a significant (3.6 fold, p<0.001) reduction in EZH2-induced cell invasion (FIG. 4D).

Figure 12:
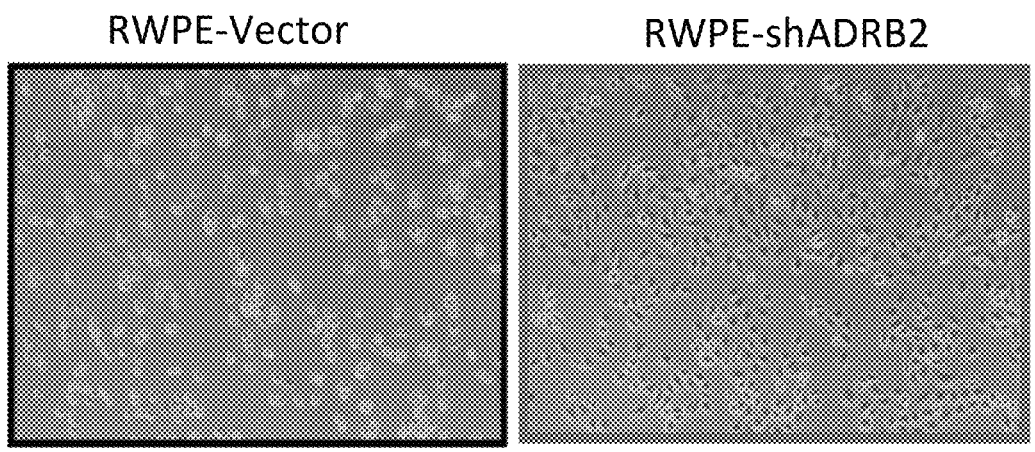
FIG. 12 shows that stable RWPE-shADRB2 cells have more transformed morphology than vector control.

The stable RWPE-shADRB2 cells were examined for other malignant phenotypes besides cell invasion and migration. It was observed that the RWPE-shADRB2 cells display a mesenchymal phenotype with fibroblast-like shape, whereas the vector control cells appear more rounded (FIG. 12). This morphological conversion highly resembles the converse of the mesenchymal-to-epithelial transition by constitutively active Rap1A, a primary downstream effector of β-adrenergic signaling (Price et al., J Biol Chem 279, 35127-35132 2004). To confirm that ADRB2 inhibition in fact transformed the RWPE benign prostate epithelial cells, the expression of typical mesenchymal biomarkers and adhesion molecules was examined. Immunoblot analysis demonstrated markedly increased expression in mesenchymal cell biomarkers, vimentin and N-cadherin, and yet a significant decrease of the expression of adhesion molecules, β-catenin and integrin beta 4 (ITGB4) (FIG. 4E). No significant changes in E-cadherin expression were observed. Antagonist (ICI 118,551)-mediated inactivation of ADRB2 recaptured the expressional changes in RWPE-shADRB2 cells (FIG. 4F). To investigate whether this property of ADRB2 has a link to EZH2 function, EZH2 was overexpressed in native RWPE cells. EZH2 overexpression evoked expressional changes analogous to the inhibition of ADRB2. Re-activation of ADRB2 in the EZH2-overexpressing RWPE cells was able to reverse the effect induced by EZH2 overexpression.

ADRB2 Inhibits Prostate Tumor Growth In Vivo

Figure 5:
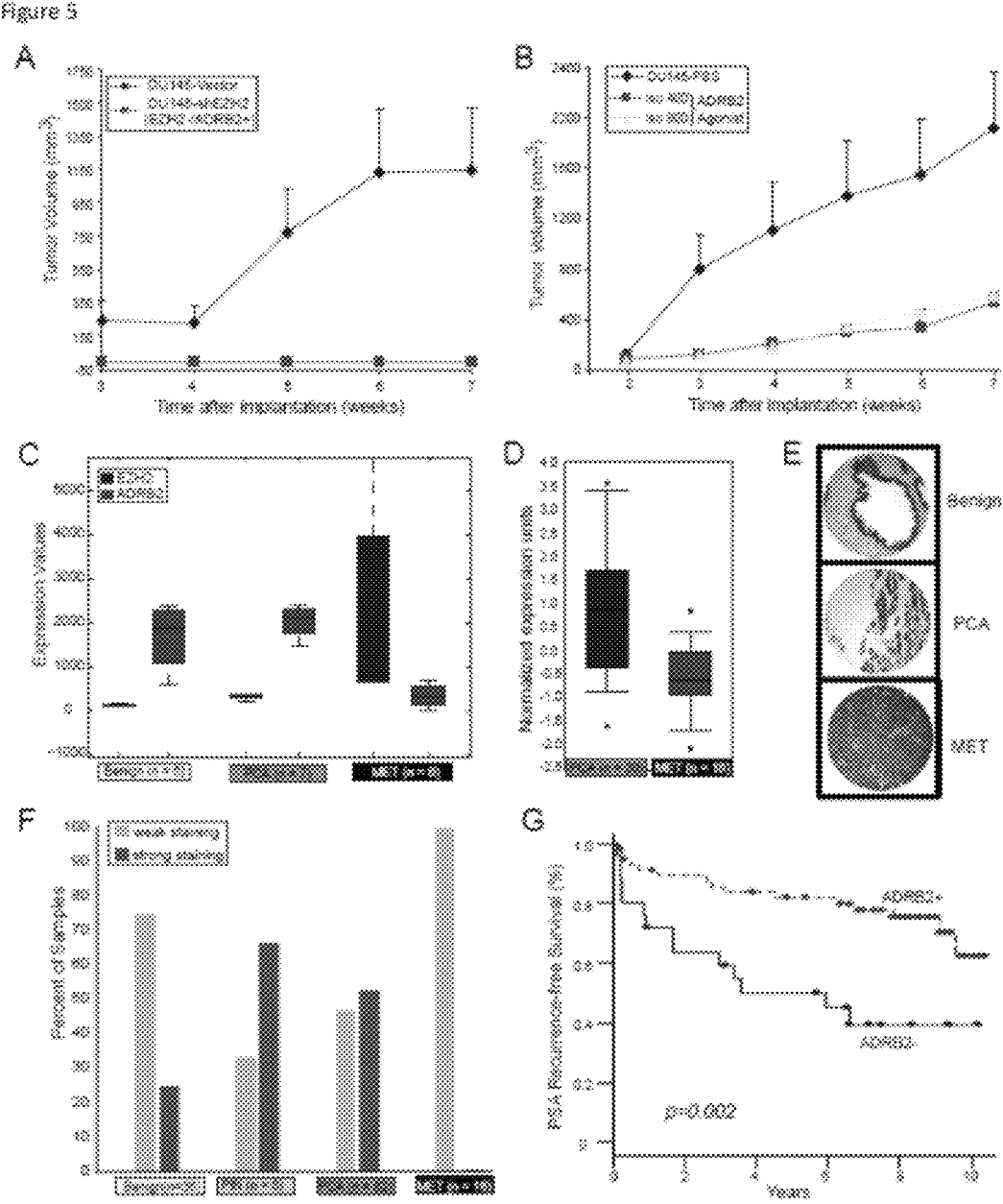
FIG. 5 shows that ADRB2 expression correlates with prostate cancer progression. (A) The stable DU145-shEZH2 (EZH2−/ADRB2+) cells have inhibited tumor growth in a xenograft mouse model. (B) ADRB2 activation inhibits tumor growth in a xenograft mouse model. (C) Affymetrix microarray analysis of grossly dissected tissues including 6 benign, 7 clinically localized (PCA) and 6 metastatic prostate cancer (METs) tissues. (D) cDNA microarray analysis of laser capture microdissected (LCM) prostate cancer epithelial cells for ADRB2 expression. (E) Representative immunostaining of ADRB2 in benign prostate, localized (PCA) and metastastic (MET) prostate cancer. (F) Histogram of ADRB2 immunostaining as assessed using prostate cancer tissue microarray analysis (TMA). (G) Kaplan-Meier analysis shows that individuals with clinically localized PCA that have lower expression of ADRB2 (low intensity and low percentage of staining) have a greater risk for disease recurrence after prostatectomy (p=0.002).

A role for β-adrenergic signaling in cell migration, invasion and transformation was demonstrated by using in vitro cell line models. The studies were thus extended to in vivo mouse models. The effect of stable EZH2 knockdown, leading to consequent ADRB2 induction (FIG. 2E), on prostate tumor formation was assayed by inoculating the EZH2−/ADRB2+ DU145-shEZH2 cells into nude mice. Tumors developed in all control EZH2+/ADRB2− mice at 3 weeks after injection, whereas the EZH2−/ADRB2+ mice did not grow tumors by 7 weeks after injection (FIG. 5A).

To directly examine the effect of ADRB2 in in vivo prostate tumor growth, native DU145 prostate cancer cells were subcutaneously injected into nude mice. These mice were then randomly separated into 3 groups (5 mice per group), and treated, through intraperitoneal injections, with either PBS or the ADRB2 agonist isoproterenol at 400 μg/day or 800 ug/day. Xenograft tumors started to grow at 2 weeks after implantation. When compared with the PBS-treated control group, isoproterenol-treated mice developed significantly (two-sample t-test, p=0.006) smaller tumors (FIG. 5B).

ADRB2 Protein Level Predicts Prostate Cancer Clinical Outcome

The repression of ADRB2 by oncogenic EZH2 and its implication in cell invasion and tumorigenesis in both in vitro and in vivo models suggest that reduced expression of ADRB2 may be associated with human prostate cancer progression. To assess ADRB2 expression during human prostate cancer progression, a prostate cancer microarray study (Varambally et al., Cancer Cell 8, 393-406 2005) that profiled 6 benign prostate tissue samples, 7 clinically localized prostate cancers and 6 metastatic prostate cancers was examined. It was found that ADRB2 transcript is strongly repressed (p=0.003 by t-test) in the metastatic samples, being inversely associated (r=−0.85, p<0.0001) with EZH2 expression (FIG. 5C). It is possible that ADRB2 may present in the stromal cells and its down-regulation in metastatic prostate cancer merely reflects the decrease in the percentage of stroma. To exclude this possibility, ADRB2 expression was examined in a prostate cancer microarray profiling dataset using laser capture microdissected (LCM) epithelial cells (Tomlins et al., Nat Genet 39, 41-51 2007). cDNA microarray analysis of 30 LCM PCA and 16 MET samples confirmed down-regulation (p<0.001 by t-test) of ADRB2 in metastatic prostate cancer (FIG. 5D).

To evaluate ADRB2 protein expression in prostate tumors, ADRB2 immunohistochemistry was performed in 36 benign, 6 prostatic intraepithelial neoplasia (PIN), 82 clinically localized PCA, and 16 MET tissues. ADRB2 staining was primarily observed in epithelial cells (FIG. 5E). Overall, there was a significant difference in the distribution of median ADRB2 staining intensity among the 4 groups (p<0.0001 by Kruskal-Wallis test). The metastatic tumors had the weakest expression of ADRB2. Most cases of low or absent ADRB2 staining were observed in METs (FIG. 5E-F). The present invention is not limited to a particular mechanism. Indeed, an understanding of the mechanism is not necessary to practice the present invention. Nonetheless, these results led to the hypothesis that low ADRB2 protein levels may portend the aggressiveness of clinically localized prostate cancer. This would be in contrast to high EZH2 levels being indicative of poor clinical outcome in patients with clinically localized disease (Varambally et al., Nature 419, 624-629 2002).

The clinical outcome of the 82 patients with organ-confined prostate cancer was next examined, taking into account clinical and pathological parameters. By Kaplan-Meier analysis, a low product score (<240) indicative of low ADRB2 staining was significantly (p=0.002) associated with clinical failure, in comparison with high product score (>=240) indicative of strong ADRB2 staining (FIG. 5G). Multivariate Cox proportional-hazards regression analysis revealed that ADRB2 could predict clinical failure independently of Gleason score, maximum tumor dimension, surgical margin status, and preoperative PSA (Table 1). With an overall recurrence ratio of 3.4 (95% CI: 1.5-7.8, p=0.004), it was by far the strongest predictor of clinical failure in this model. In order to compare the ability of ADRB2 status to predict outcomes beyond that given with standard clinical parameters, ADRB2 was compared with a preoperative nomogram for predicting treatment failure at 5 years (Kattan et al., J Natl Cancer Inst 90, 766-771 1998). As shown in Table 2, ADRB2 provides significant predictive power for patient prognosis (p=0.015, recurrence ratio=2.7, 95% CI: 1.2-6.0) that is both independent of the preoperative nomogram and of greater significance. Taken together, ADRB2 is down-regulated in metastatic prostate cancer, low ADRB2 expression is associated with poor prognosis of clinically localized prostate cancer, and ADRB2 expression provides additional prognostic information beyond a typical clinical nomogram.

TABLE 1

Multivariate Cox regression analysis of association of ADRB2 and clinical parameters with cancer recurrence.

| | Recurrence Ratio | 95% CI | | P |
|---|---|---|---|---|
| ADRB2 (Product score >= 240 vs. <240) | 3.423 | 1.500 | 7.808 | 0.004 |
| Gleason (>=7 vs. <= 6) | 1.604 | 0.607 | 4.241 | 0.341 |
| Tumor size (>=2 cm vs. <2 cm) | 1.306 | 0.526 | 3.239 | 0.565 |
| Surgical Margin (Positive vs. Negative) | 1.737 | 0.807 | 3.740 | 0.158 |
| Pre-operative PSA (>7, 4-7, <=4) | 1.519 | 0.852 | 2.707 | 0.156 |

Note:
Sample size is 82 with 29 recurrences. Product score indicates the product of ADRB2 intensity measure (range: 1, 2, 3, and 4) and percentage of staining measure (range: 0-100).

TABLE 2

Multivariate Cox regression analysis of association of ADRB2 and preoperative nomogram with cancer recurrence.

| | Recurrence Ratio | 95% CI | | P |
|---|---|---|---|---|
| ADRB2 (Product score >=240 vs. <240) | 2.694 | 1.212 | 5.989 | 0.015 |
| Preoperative nomogram for 5-year recurrence-free prediction | 1.019 | 1.003 | 1.036 | 0.020 |
| Tumor size (>=2 cm vs. <2 cm) | 1.146 | 0.470 | 2.791 | 0.764 |
| Surgical Margin (Positive vs. Negative) | 1.612 | 0.736 | 3.531 | 0.233 |
| Age | 1.009 | 0.960 | 1.061 | 0.716 |

TABLE 3

| Gene Symbol | siRNA pval | adeno pval |
|---|---|---|
| SFRP1 | 0.0000 | 0.0271 |
| SPRR1B | 0.0000 | 0.0427 |
| SPUVE | 0.0000 | 0.0281 |
| IGFBP2 | 0.0001 | 0.0024 |
| SERPINE1 | 0.0000 | 0.0009 |
| GM2A | 0.0005 | 0.0027 |
| PSMD3 | 0.0003 | 0.0003 |
| ARL7 | 0.0001 | 0.0062 |
| CCND1 | 0.0000 | 0.0107 |
| CCNG2 | 0.0000 | 0.0069 |
| CALR | 0.0005 | 0.0309 |
| LOC127262 | 0.0000 | 0.0044 |
| THBS1 | 0.0001 | 0.0110 |
| CD59 | 0.0003 | 0.0006 |
| PXN | 0.0000 | 0.0493 |
| ANGPT2 | 0.0000 | 0.0184 |
| FLJ12443 | 0.0002 | 0.0477 |
| ST14 | 0.0000 | 0.0048 |
| ATP1A1 | 0.0312 | 0.0010 |
| ATP1A1 | 0.0036 | 0.0010 |
| JUP | 0.0000 | 0.0060 |
| HIPK2 | 0.0000 | 0.0319 |
| PAK6 | 0.0000 | 0.0126 |
| ZDHHC3 | 0.0000 | 0.0155 |
| KCTD2 | 0.0000 | 0.0019 |
| TMEM9 | 0.0139 | 0.0035 |
| ICMT | 0.0271 | 0.0009 |
| HIF1AN | 0.0000 | 0.0053 |
| COL4A2 | 0.0000 | 0.0012 |
| ANKH | 0.0000 | 0.0305 |
| CRIP2 | 0.0000 | 0.0015 |
| ITGB5 | 0.0000 | 0.0003 |
| LAD1 | 0.0009 | 0.0114 |
| FLJ10700 | 0.0000 | 0.0282 |
| LOC169611 | 0.0000 | 0.0029 |
| NBL1 | 0.0258 | 0.0206 |
| AQP3 | 0.0001 | 0.0000 |
| MLF2 | 0.0003 | 0.0069 |
| PAFAH1B3 | 0.0001 | 0.0025 |
| KCNS1 | 0.0000 | 0.0172 |
| SIAT1 | 0.0000 | 0.0272 |
| ALDH4A1 | 0.0026 | 0.0008 |
| ALDH4A1 | 0.0001 | 0.0008 |
| MGC4692 | 0.0003 | 0.0258 |
| DDOST | 0.0079 | 0.0130 |
| E2IG4 | 0.0000 | 0.0486 |
| SNCG | 0.0000 | 0.0181 |
| SNCG | 0.0000 | 0.0181 |
| SNRPD2 | 0.0000 | 0.0029 |
| ALDOB | 0.0022 | 0.0426 |
| SLC35B2 | 0.0000 | 0.0024 |
| DKFZP434J154 | 0.0000 | 0.0381 |
| FLJ10700 | 0.0000 | 0.0295 |
| AIP | 0.0022 | 0.0052 |
| RNASET2 | 0.0003 | 0.0207 |
| CRIP1 | 0.0001 | 0.0308 |
| TMPIT | 0.0007 | 0.0132 |
| KNSL8 | 0.0001 | 0.0499 |
| PTPRE | 0.0000 | 0.0311 |
| MGC10540 | 0.0000 | 0.0100 |
| HDAC3 | 0.0000 | 0.0004 |
| LOC338692 | 0.0002 | 0.0058 |
| EFNB1 | 0.0180 | 0.0384 |
| LOC254531 | 0.0003 | 0.0094 |
| CD44 | 0.0003 | 0.0121 |
| HGF | 0.0001 | 0.0030 |
| GSN | 0.0488 | 0.0059 |
| ANKRD9 | 0.0499 | 0.0421 |
| MGC3123 | 0.0002 | 0.0332 |
| RAC2 | 0.0000 | 0.0020 |
| PPT1 | 0.0001 | 0.0105 |
| CS | 0.0038 | 0.0441 |
| CD44 | 0.0011 | 0.0080 |
| ANXA7 | 0.0002 | 0.0068 |
| EVPL | 0.0013 | 0.0027 |
| EDNRB | 0.0010 | 0.0009 |
| AK1 | 0.0096 | 0.0143 |
| MTAC2D1 | 0.0213 | 0.0227 |
| PRKRIR | 0.0008 | 0.0145 |
| KLK6 | 0.0034 | 0.0149 |
| TTC5 | 0.0008 | 0.0017 |
| CRA | 0.0000 | 0.0038 |
| COL17A1 | 0.0000 | 0.0443 |
| ATP5D | 0.0028 | 0.0141 |
| HSPC111 | 0.0003 | 0.0229 |
| CTSB | 0.0144 | 0.0062 |
| SEC13L1 | 0.0012 | 0.0071 |
| FLJ12875 | 0.0004 | 0.0375 |
| DKFZP434J154 | 0.0007 | 0.0199 |
| EIF2S1 | 0.0005 | 0.0007 |
| AAMP | 0.0000 | 0.0056 |
| BCLP | 0.0038 | 0.0014 |
| ADRB2 | 0.0001 | 0.0026 |
| NUP214 | 0.0017 | 0.0048 |
| POLR2G | 0.0014 | 0.0243 |
| CD99 | 0.0349 | 0.0030 |
| ACTN1 | 0.0013 | 0.0329 |
| RGS19IP1 | 0.0037 | 0.0016 |
| CORO1C | 0.0003 | 0.0261 |
| PPP1R12B | 0.0475 | 0.0390 |
| DAG1 | 0.0002 | 0.0009 |
| PRDX5 | 0.0001 | 0.0072 |
| ANXA11 | 0.0008 | 0.0117 |
| CIT | 0.0059 | 0.0372 |
| STAT6 | 0.0046 | 0.0048 |
| BAD | 0.0012 | 0.0370 |
| FARS1 | 0.0427 | 0.0136 |

TABLE 3-continued

| Gene Symbol | siRNA pval | adeno pval |
|---|---|---|
| CTNND1 | 0.0007 | 0.0095 |
| HK1 | 0.0423 | 0.0020 |
| MPZL1 | 0.0000 | 0.0208 |
| PRDX3 | 0.0211 | 0.0427 |
| CDH3 | 0.0013 | 0.0239 |
| MGC:13379 | 0.0009 | 0.0433 |
| EPB41 | 0.0188 | 0.0413 |
| BSCL2 | 0.0140 | 0.0283 |
| BCKDHA | 0.0056 | 0.0025 |
| MAP3K10 | 0.0314 | 0.0128 |
| COL541 | 0.0045 | 0.0213 |
| BRAP | 0.0224 | 0.0381 |
| RRBP1 | 0.0254 | 0.0260 |
| RGS19IP1 | 0.0141 | 0.0074 |
| ARL3 | 0.0240 | 0.0033 |
| FLJ36525 | 0.0093 | 0.0453 |
| ATP5I | 0.0064 | 0.0208 |
| C12orf10 | 0.0200 | 0.0109 |
| MYST3 | 0.0373 | 0.0197 |
| P15RS | 0.0142 | 0.0291 |
| PTPNS1 | 0.0044 | 0.0026 |
| FLNA | 0.0390 | 0.0317 |
| HLA-DQA1 | 0.0257 | 0.0456 |
| ABP1 | 0.0051 | 0.0488 |
| NQO2 | 0.0414 | 0.0066 |
| LOC286161 | 0.0253 | 0.0269 |

TABLE 4

| Gene Symbol | Accession | SUZ12 LnCaP | SUZ12 PC3 | IgG PC3 | SUZ12-IgG PC3 |
|---|---|---|---|---|---|
| TUBB | NM_178012 | 3.188 | 3.851 | 1.706 | 2.145 |
| AQP7 | UP_12 | 1.889 | 2.575 | 1.76 | 0.815 |
| GBL | NM_022372 | 2.503 | 2.431 | 1.58 | 0.851 |
| TUBA8 | NM_018943 | 1.742 | 2.388 | 1.201 | 1.187 |
| ZNF217 | NM_006526 | 2.037 | 2.381 | 1.046 | 1.335 |
| HNMT | NM_006895 | 2.465 | 2.285 | 1.633 | 0.652 |
| PCDH11 | NM_032968 | 2.819 | 2.279 | 1.575 | 0.704 |
| ZIC1 | NM_003412 | 1.516 | 2.254 | 1.295 | 0.959 |
| GJB5 | NM_005268 | 4.16 | 2.214 | 1.357 | 0.857 |
| MXI1 | UP_155 | 3.01 | 2.206 | 1.453 | 0.753 |
| WIT-1 | NM_015855 | 2.624 | 2.195 | 1.328 | 0.867 |
| HEYL | NM_014571 | 2.896 | 2.191 | 1.468 | 0.723 |
| GAS7 | NM_005890 | 2.098 | 2.182 | 1.458 | 0.724 |
| JAK1 | NM_002227 | 2.859 | 2.145 | 1.486 | 0.659 |
| TCTEL1 | NM_006519 | 2.106 | 2.135 | 1.146 | 0.989 |
| LLT1 | NM_013269 | 1.583 | 2.132 | 1.205 | 0.927 |
| NDUFS3 | NM_004551 | 1.733 | 2.118 | 0.929 | 1.189 |
| KLK1 | NM_002257 | 2.013 | 2.094 | 1.093 | 1.001 |
| DDX15 | NM_001358 | 2.971 | 2.092 | 1.035 | 1.057 |
| CINP | IN_77 | 2.02 | 2.072 | 1.325 | 0.747 |
| XP5 | NM_014357 | 2.905 | 2.061 | 1.447 | 0.614 |
| RX | NM_013435 | 1.621 | 2.055 | 1.35 | 0.705 |
| FLJ20244 | NM_017722 | 3.169 | 2.053 | 1.288 | 0.765 |
| PRSS22 | NM_022119 | 2.314 | 2.021 | 1.362 | 0.659 |
| TYROBP | NM_003332 | 1.712 | 2.009 | 1.352 | 0.657 |
| KCNK5 | NM_003740 | 2.4 | 2.006 | 1.167 | 0.839 |
| MRS2L | NM_020662 | 2.224 | 1.967 | 1.142 | 0.825 |
| SERPINB9 | NM_004155 | 2.664 | 1.949 | 1.281 | 0.668 |
| KIAA0277 | NM_012294 | 2.243 | 1.93 | 1.32 | 0.61 |
| PTPRZ1 | NM_002851 | 1.854 | 1.918 | 1.098 | 0.82 |
| LOC51143 | NM_016141 | 1.858 | 1.904 | 1.112 | 0.792 |
| CYB5 | NM_001914 | 1.862 | 1.886 | 1.083 | 0.803 |
| TSSC3 | NM_003311 | 1.837 | 1.88 | 1.215 | 0.665 |
| BIRC6 | NM_016252 | 1.755 | 1.876 | 1.175 | 0.701 |
| CTAGE-1 | NM_022663 | 1.502 | 1.872 | 1.111 | 0.761 |
| LHX6 | NM_014368 | 2.007 | 1.865 | 1.145 | 0.72 |
| SPR | NM_003124 | 2.157 | 1.857 | 1.07 | 0.787 |
| CSNK1G2 | NM_001319 | 1.516 | 1.847 | 1.218 | 0.629 |
| LOC56902 | NM_020143 | 1.675 | 1.831 | 0.814 | 1.017 |
| CLDN17 | NM_012131 | 2.561 | 1.819 | 1.144 | 0.675 |
| DGUOK | NM_001929 | 4.105 | 1.812 | 0.668 | 1.144 |
| FDXR | NM_004110 | 3.964 | 1.798 | 0.819 | 0.979 |
| HRC | NM_002152 | 2.692 | 1.798 | 1.065 | 0.733 |
| GP1BB | NM_000407 | 1.793 | 1.763 | 0.759 | 1.004 |
| GTF3C1 | NM_001520 | 2.36 | 1.756 | 0.974 | 0.782 |
| KCNN3 | NM_002249 | 1.766 | 1.747 | 0.981 | 0.766 |
| FANCG | NM_004629 | 1.546 | 1.737 | 0.915 | 0.822 |
| DCI | NM_001919 | 1.607 | 1.724 | 0.866 | 0.858 |
| ADRB2 | NM_000024 | 1.918 | 1.717 | 0.532 | 1.165 |
| DFFA | NM_004401 | 1.557 | 1.717 | 0.773 | 0.944 |
| IL22 | NM_020525 | 1.956 | 1.715 | 1.096 | 0.619 |
| MN1 | NM_002430 | 2.81 | 1.649 | 0.888 | 0.761 |
| ECGF1 | NM_001953 | 1.917 | 1.647 | 0.881 | 0.766 |
| DKFZP564B167 | NM_015415 | 2.037 | 1.645 | 1.029 | 0.616 |
| PNLIPRP1 | NM_006229 | 1.775 | 1.643 | 0.667 | 0.976 |
| SERPINF2 | NM_000934 | 2.017 | 1.618 | 0.956 | 0.662 |
| KCNE1 | NM_000219 | 1.852 | 1.618 | 0.935 | 0.683 |
| HEBP | NM_015987 | 2.594 | 1.613 | 0.916 | 0.697 |
| H3F3A | NM_002107 | 2.606 | 1.6 | 0.758 | 0.842 |
| IFNA6 | NM_021002 | 2.363 | 1.584 | 0.778 | 0.806 |
| RPL10A | NM_007104 | 1.573 | 1.584 | 0.676 | 0.908 |
| IGFBP2 | NM_000597 | 1.911 | 1.556 | 0.842 | 0.714 |
| SUPT6H | IN_143 | 2.77 | 1.515 | 0.155 | 1.36 |

TABLE 5

| SEQ ID NO | Gene | Primer | Sequence | Length | Experiment |
|---|---|---|---|---|---|
| 1 | ADRB2 | pF2 | CCTGGGTATTCCAGTTCCAG | 396 | ChIP-PCR |
| 2 | ADRB2 | pR2 | CAGGGTTTGATTTCCCATGT | 396 | ChIP-PCR |
| 3 | ADRB2 | F10 | TTCCTCTTTGCATGGAATTTG | 241 | qRT-PCR |
| 4 | ADRB2 | R10 | AGAGGAGTGGGGGAAGAGTC | 241 | qRT-PCR |
| 5 | GAPDH | F1 | TGCACCACCAACTGCTTAGC | 87 | qRT-PCR |
| 6 | GAPDH | R1 | GGCATGGACTGTGGTCATGAG | 87 | qRT-PCR |
| 7 | CNR1 | pF1 | GCAGAGCTCTCCGTAGTCAG | 269 | ChIP-PCR |
| 8 | CNR1 | pR1 | AACAGGCTGGGGCCATACAG | 269 | ChIP-PCR |
| 9 | MYT1 | pF1 | AGGCACCTTCTGTTGGCCGA | 350 | ChIP-PCR |
| 10 | MYT1 | pR1 | AGGCAGCTGCCTCCCGTACA | 350 | ChIP-PCR |
| 11 | ACTIN | pF1 | AGTGTGGTCCTGCGACTTCTAAG | 77 | ChIP-PCR |
| 12 | ACTIN | pR1 | CCTGGGCTTGAGAGGTAGAGTGT | 77 | ChIP-PCR |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method for identifying risk of prostate cancer recurrence in a prostate cancer patient, comprising:
   a) detecting the level of expression of Adrenergic Receptor, Beta 2 (ADRB2) polypeptide compared to normal expression of ADRB2 polypeptide in a prostate cancer biopsy sample from a patient diagnosed with prostate cancer by detecting the binding of an antibody that specifically binds to an ADRB2 polypeptide using an immunoassay;
   b) comparing the level of expression of ADRB2 polypeptide in said sample to the level in a sample of normal prostate tissue; and
   c) identifying said patient as being at risk of recurrence of prostate cancer when said expression level is decreased relative to the level in normal prostate tissue.

2. The method of claim 1, wherein said recurrence of disease after prostatectomy comprises development of metastatic cancer.

* * * * *